US011326209B2

(12) United States Patent
Jacobson et al.

(10) Patent No.: US 11,326,209 B2
(45) Date of Patent: May 10, 2022

(54) CELL-BASED GENOMIC RECORDED ACCUMULATIVE MEMORY

(71) Applicants: Massachusetts Institute of Technology, Cambridge, MA (US); Whitehead Institute for Biomedical Research, Cambridge, MA (US)

(72) Inventors: Joseph M. Jacobson, Newton, MA (US); Noah Jakimo, Boston, MA (US); Naama Kanarek, Brighton, MA (US); David Sabatini, Cambridge, MA (US)

(73) Assignees: Massachusetts Institute of Technology, Cambridge, MA (US); Whitehead Institute of Biomedical Research, Cambridge, MA (US)

( * ) Notice: Subject to any disclaimer, the term of this patent is extended or adjusted under 35 U.S.C. 154(b) by 819 days.

(21) Appl. No.: 14/536,128

(22) Filed: Nov. 7, 2014

(65) Prior Publication Data
US 2015/0133315 A1 May 14, 2015

Related U.S. Application Data

(60) Provisional application No. 61/901,418, filed on Nov. 7, 2013.

(51) Int. Cl.
| | |
|---|---|
| C12Q 1/6874 | (2018.01) |
| C12Q 1/6897 | (2018.01) |
| G06N 3/12 | (2006.01) |
| C12N 15/70 | (2006.01) |
| C12N 15/10 | (2006.01) |
| C12N 15/63 | (2006.01) |

(52) U.S. Cl.
CPC ........... *C12Q 1/6874* (2013.01); *C12N 15/70* (2013.01); *C12Q 1/6897* (2013.01); *G06N 3/123* (2013.01); *C12N 15/102* (2013.01); *C12N 15/63* (2013.01)

(58) Field of Classification Search
CPC .................................................. C12N 15/102
See application file for complete search history.

(56) References Cited

U.S. PATENT DOCUMENTS

| | | | | |
|---|---|---|---|---|
| 8,697,359 | B1* | 4/2014 | Zhang | C12N 15/85 424/94.1 |
| 2005/0069921 | A1 | 3/2005 | Roth et al. | |
| 2006/0024733 | A1 | 2/2006 | Wong et al. | |
| 2011/0145940 | A1* | 6/2011 | Voytas | C12N 9/22 800/13 |
| 2011/0203012 | A1* | 8/2011 | Dotson | C12N 15/8257 800/278 |
| 2014/0068797 | A1* | 3/2014 | Doudna | C12N 15/90 800/18 |
| 2014/0273231 | A1 | 9/2014 | Zhang et al. | |
| 2015/0259684 | A1* | 9/2015 | Church | C07K 2/00 435/462 |

FOREIGN PATENT DOCUMENTS

WO 2012017329 A2 2/2012

OTHER PUBLICATIONS

Gasiunas et al., PNAS Plus, 2012, pp. E2579-E2586.*
UCSC Genome Browser (BLAT result for hAAVS1 reference sequence provided by Mali, accessed on Sep. 8, 2020, 3 pages) (Year: 2020).*
Mali et al. (2013) RNA-Guided Human Genome Engineering via Cas9. Science, 339:823-826, supplementary materials) (Year: 2013).*
Mao et al. (2009) DNA Repair by Homologous Recombination, But not By Nonhomologous End Joining, is Elevated in Breast Cancer Cells. Neoplasia, 11(7):683-691 (Year: 2009).*
Goeddel, D.V., "The Principles of Good Expression," Gene Expression Technology, Methods in Enzymology, 185, 1990.
Amann, E., et al., "Tightly Regulated tac Promotor Vectors Useful for the Expression of Unfused and Fused Proteins in *Escherichia coli*," Gene 69(2), pp. 301-315 (Sep. 1988).
Studier, F. W., et al., "Use of T7 RNA Polymerase to Direct Expression of Cloned Genes," Methods in Enzymology vol. 185, pp. 60-89 (1990).
Auditore, L., et al., "Theoretical Estimation of 64Cu Production with Neutrons Emitted During 18F Production with a 30meV Medical Cyclotron," Applied Radiation and Isotopes 122: 229-234 (2017).
Kurjan, J., Herskowitz, I., "Structure of a Yeast Pheromone Gene (MFx): A Putative α-Factor Precursor Contains Four Tandem Copies of Mature α-Factor," Cell, vol. 30, pp. 933-943 (1982).
Schultz, L.D., et al., "Expression and Secretion in Yeast of a 400-kDa Envelope Glycoprotein Derived from Epstein-Barr Virus," Gene, vol. 54, pp. 113-123 (1987).
Seed, B., "An LFA-3 cDNA Encodes a Phospholipid-Linked Membrane Protein Homologous to its Receptor CD2," Nature, vol. 329, p. 842(1987).
Kaufman, R.J., et al., "Translational Efficiency of Polycistronic mRNAs and Their Utilization to Express Heterologous Genes in Mammalian Cells," The EMBO Journal 6(1): 187-193 (1987).
Sambrook, et al., Molecular Cloning: A Laboratory Manual, 2nd Edition, vol. 1-2 Cold Spring Harbor Laboratory, Cold Spring Harbor Laboratory Press (1989).
Mali, P., et al., "RNA-Guided Human Genome Engineering via Cas9," Science 339: 823-826 (2013).
Anderson, W.F., "Human Gene Therapy," Science 256: 808-813 (1992).
Miller, D., "Human Gene Therapy Comes of Age," Nature 357: 455-460 (1992).

(Continued)

*Primary Examiner* — Neil P Hammell
(74) *Attorney, Agent, or Firm* — Elmore Patent Law Group, P.C.; Joseph Zucchero; Carolyn Elmore

(57) ABSTRACT

The present invention relates to a cell based genomic Recorded Accumulative Memory (geRAM) system (also referred to herein as Genomically Encoded Memory (GEM)) for recoding data (i.e., changes in nucleic acid sequences in cellular DNA in response to physical and/or chemical signal (s)) from the cellular environment.

9 Claims, 18 Drawing Sheets
Specification includes a Sequence Listing.

(56) References Cited

OTHER PUBLICATIONS

Van Brunt, J., "Molecular Farming: Transgenic Animals as Bioreactors," Biotechnology 6(10): pp. 1149-1154 (1988).
Vigne, E., et al., "Third-Generation Adenovectors for Gene Therapy," Restorative Neurology and Neuroscience, vol. 8, pp. 35-36 (1995).
Kremer, E.J., Perricaudet, M., "Adenovirus and Adeno-Associated Virus Mediated Gene Transfer," British Medical Bulletin 51(1); pp. 31-44 (1995) Abstract only.
Haddada, H., et al., "Gene Therapy Using Adenovirus Vectors," Current Topics in Microbiology and Immunology, pp. 297-306, (1995).
Yu, et al., "Progress Towards Gene Therapy for HIV Infection," Gene Therapy, vol. 1, pp. 13-26 (1994) Abstract only.
Terns, M.P., et al., "CRISPR-Based Adaptive Immune Systems," Current Opinion in Microbiology vol. 14, pp. 321-327 (2011).
Ran, F.A., et al., "Double Nicking by RNA-Guided CRISPR Cas9 for Enhanced Genome Editing Specificity," Cell, vol. 154, pp. 1380-1389 (2013).
Wiedenheft, B., et al., "RNA-Guided Genetic Silencing Systems in Bacteria and Archaea," Nature 482: 331-338 (2012).
Bhaya, D., et al., "CRISPR-Cas Systems in Bacteria and Archaea: Versatile Small RNAs for Adaptive Defense and Regulation," Annu. Rev. Genet. 45: 273-297 (2011).
Jinek, M., et al., "A Programmable Dual-RNA-Guided DNA Endonuclease in Adaptive Bacterial Immunity," Science 337: 816-821 (2012).
Farzadfard, F., et al., "Genomically encoded analog memory with precise in vivo DNA writing in living cell populations," Research 346(issue 6211): Nov. 2014.
Jiang, W., et al., "Demonstration of CRISPR/Cas9/sgRNA-mediated targeted gene modification in *Arabidopsis*, tobacco, sorghum and rice," Nucleic Acids Research, 41(20): pp. 1-12 (2013).
Siuti, et al., "Synthetic Circuits Integrating Logic and Memory in Living Cells," Nature Biotechnology, vol. 31, pp. 448-452, Feb. 2013.

\* cited by examiner

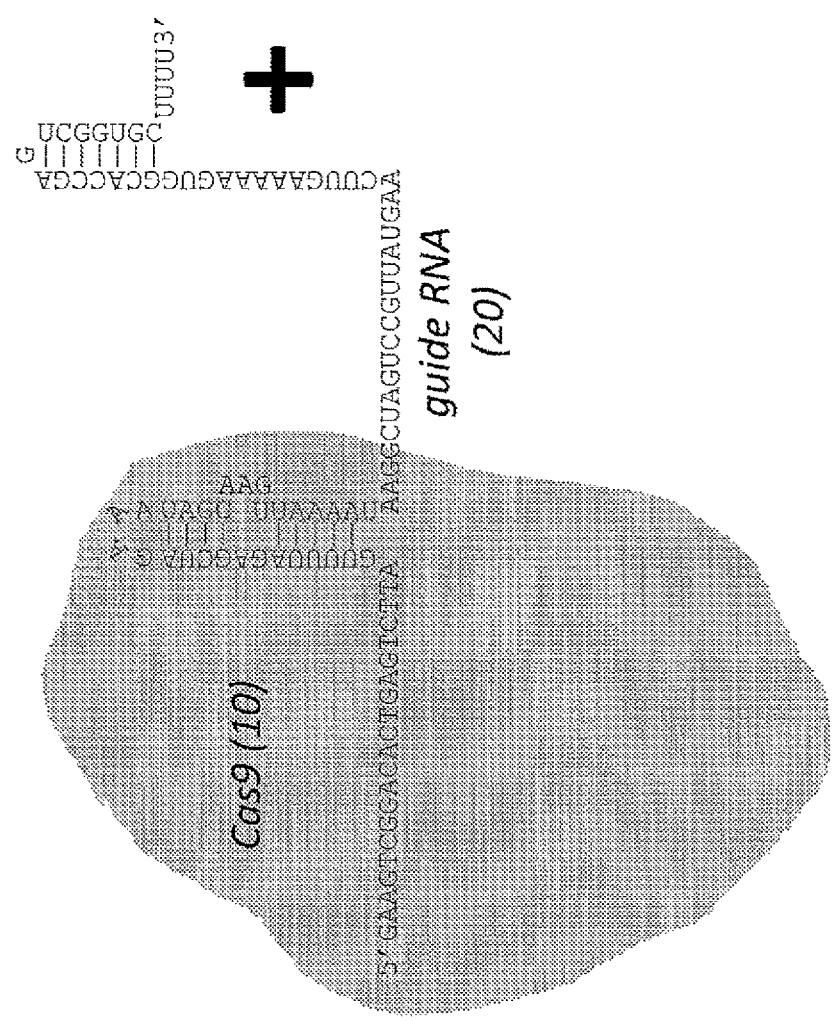

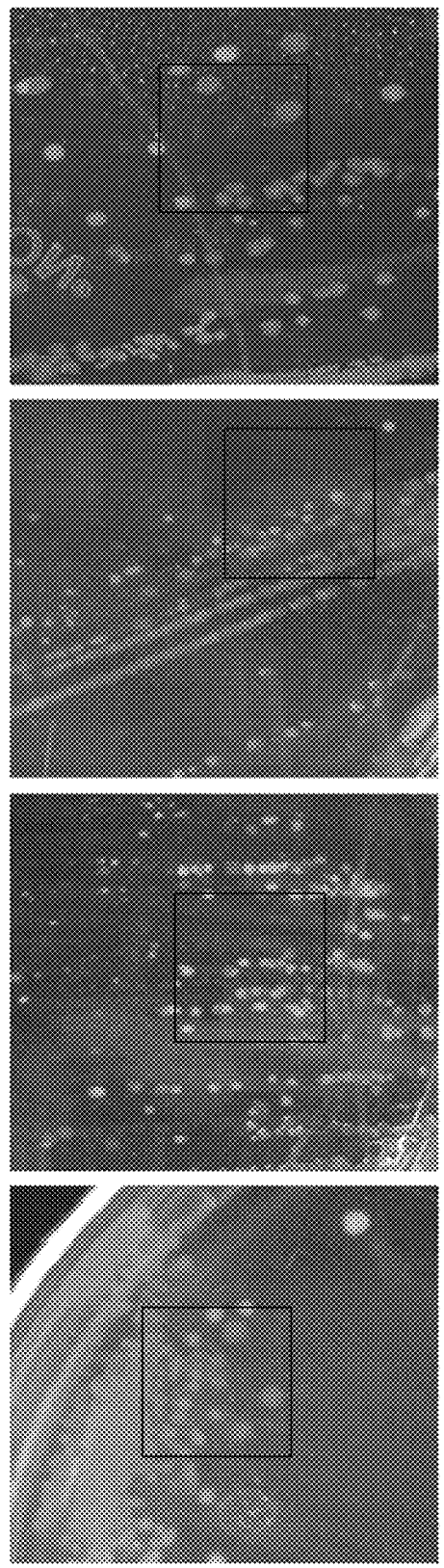
| Time Induced minutes | 0 minutes | 5 minutes | 10 | 15 minutes |
|---|---|---|---|---|
| Within ROI Box | | | | |
| #GFP+ Colonies | ~40 | 25 | | 22 |
| #GFP- Colonies | 7 | 3 | | ~40 |
| | | 9 | | |
| | | 15 | | |
| %GFP+ | 85 | 73 | | 55 |
| | | 16 | | |
FIG 6

FIG 9

GCTCTGTATAAGGAGCCTCGGAAGGTGCATGCTGGAAGCCTCTGTATAAGGAGCCTCGGAAGGTGCATGCTGGAAG...

⇨ Check for perfect match

Lookup Table 1 of Perfect Repeats
GCTCTGTATAAGGAGCCTCGAAGGTGCATGCTGGAA
GCTCTGTATAAGGAGCCTTGGAAGGTGCATGCTGGAA
GCTCTGTATAAGGAGCCTTGGAAGGTGCATGCTGGAA
GCTCTGTATAAGGAGCCTTGGAAGGTGTATGCTGGAA
GCTCTGTATAAGGAGCCTCTTAAGGTGCACGTTGTAA → No indel ⇨ If no nearly perfect match

Lookup Table 2 of Indel Mutated Repeats
CTCTGTATAAGGAGCCTCGGAAGGTGCATGCTGGAAG
: :
GACTCTGTATAAGGAGCCTTCGGAAGGTGCATGCTGGA
: : :
: : :

→ −1 deletion at pos 1
→ +1 insertion at pos 2

⇧ If no indel match

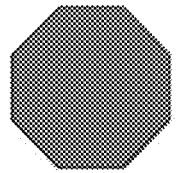

FIG 13

SEQUENCE LISTING

<160> NUMBER OF SEQ ID NOS: 18

<210> SEQ ID NO 1
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gaagtcggac actgagtctt aguuuuagag cuagaaauag caaguuaaaa uaaggcuagu    60
ccguuaugaa cuugaaaaag uggcaccgag ucggugcuuu u                       101

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: modified_base
<222> LOCATION: (32)..(38)
<223> OTHER INFORMATION: a, c, t, g, unknown or other

<400> SEQUENCE: 2
nnnnnnnnaa gtcggacact gagtcttang gnnnnnnn                            38

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(49)
<223> OTHER INFORMATION: a, c, t, g, unknown or other

<400> SEQUENCE: 3
nnnnnnnnnn nnnaagtcgg acactgagtc ttanggnnnn nnnnnnnn                 49

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (1)..(8)
<223> OTHER INFORMATION: a, c, t, g, unknown or other

<400> SEQUENCE: 4
nnnnnnnnaa gtcggacact gagtct                                              26

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(12)
<223> OTHER INFORMATION: a, c, t, g, unknown or other

<400> SEQUENCE: 5
tanggnnnnn nn                                                             12

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (31)..(37)
<223> OTHER INFORMATION: a, c, t, g, unknown or other

<400> SEQUENCE: 6
nnnnnnnnaa gtcggacact gagtctangg nnnnnnn                                  37

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(19)
<223> OTHER INFORMATION: a, c, t, g, unknown or other

<400> SEQUENCE: 7
gagaaatact agatgcgnng aggttgagaa c                                        31

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(27)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other

<400> SEQUENCE: 8
gagaaatact anatgcganc ngannnnan                                   29

<210> SEQ ID NO 9
<211> LENGTH: 2982
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gctctgtata aggagccttg gaaggtgcat gctggaagct ctgtataagg agccttggaa    60
ggtgtatgct ggaagctctg tataaggagc cttggaaggt gcatgctgga agctctgtat   120
aaggagcctt ggaaggtgca tgctggaagc tctgtataag gagccttgga aggtgcatgc   180
tggaagctct gtataaggag ccttggaagg tgcatgctgg aagctctgta taaggagcct   240
tggaaggtgc atgctggaag ctctgtataa ggagccttgg aaggtgcatg ctggaagctc   300
tgtataagga gcctcggaag gtgcatgctg gaagctctgt ataaggagcc ttggaaggtg   360
catgctggaa gctctgtata aggagcctcg gaaggtgcat gctggaagct ctgtataagg   420
agcctcggaa ggtgcatgct ggaagctctg tataaggagc ctcggaaggt gcatgctgga   480
agctctgtat aaggagcctc ggaaggtgca tgctggaagc tctgtataag gagcctcgga   540
aggtgcatgc tggaagctct gtataaggag cctcggaagg tgcatgctgg aagctctgta   600
taaggagcct cggaaggtgc atgctggaag ctctgtataa ggagcctcgg aaggtgcatg   660
ctggaagctc tgtataagga gcctcggaag gtgcatgctg gaagctctgt ataaggagcc   720
tcggaaggtg catgctggaa gctctgtata aggagcctcg gaaggtgcat gctggaagct   780
ctgtataagg agcctcggaa ggtgcatgct ggaagctctg tataaggagc ctcggaaggt   840
gcatgctgga agctctgtat aaggagcctc ggaaggtgca tgctggaagc tctgtataag   900
gagcctcgga aggtgcatgc tggaagctct gtataaggag cctcggaagg tgcatgctgg   960
aagctctgta taaggagcct cggaaggtgc atgctggaag ctctgtataa ggagcctcgg  1020
aaggtgcatg ctggaagctc tgtataagga gcctcggaag gtgcatgctg gaagctctgt  1080
ataaggagcc tcggaaggtg catgctggaa gctctgtata aggagcctcg gaaggtgcat  1140
gctggaagct ctgtataagg agcctcttaa ggtgcacgtt gtaagctctg tataaggagc  1200
ctcggaaggt gcatgctgga agctctgtat aaggagcctc ggaaggtgca tgctggaagc  1260
tctgtataag gagcctcgga aggtgcatgc tggaagctct gtataaggag cctcggaagg  1320
```

```
tgcatgctgg aagctctgta taaggagcct cggaaggtgc atgctggaag ctctgtataa    1380
ggagcctcgg aaggtgcatg ctggaagctc tgtataagga gcctcggaag gtgcatgctg    1440
gaagctctgt ataaggagcc tcggaaggtg catgctggaa gctctgtata aggagcctcg    1500
gaaggtgcat gctggaagct ctgtataagg agcctcggaa ggtgcatgct ggaagctctg    1560
tataaggagc tcggaaggt gcatgctgga agctctgtat aaggagcctc ggaaggtgca    1620
tgctggaagc tctgtataag gagcctcgga aggtgcatgc tggaagctct gtataaggag    1680
cctcggaagg tgcatgctgg aagctctgta taaggagcct cggaaggtgc atgctggaag    1740
ctctgtataa ggagcctcgg aaggtgcatg ctggaagctc tgtataagga gcctcggaag    1800
gtgcatgctg gaagctctgt ataaggagcc tcggaaggtg catgctggaa gctctgtata    1860
aggagcctcg gaaggtgcat gctggaagct ctgtataagg agcctcggaa ggtgcatgct    1920
ggaagctctg tataaggagc tcggaaggt gcatgctgga agctctgtat aaggagcctc    1980
ggaaggtgca tgctggaagc tctgtataag gagcctcgga aggtgcatgc tggaagctct    2040
gtataaggag cctcggaagg tgcatgctgg aagctctgta taaggagcct cggaaggtgc    2100
atgctggaag ctctgtataa ggagcctcgg aaggtgcatg ctggaagctc tgtataagga    2160
gcctcggaag gtgcatgctg gaagctctgt ataaggagcc tcggaaggtg catgctggaa    2220
gctctgtata aggagcctcg gaaggtgcat gctggaagct ctgtataagg agcctcggaa    2280
ggtgcatgct ggaagctctg tataaggagc tcggaaggt gcatgctgga agctctgtat    2340
aaggagcctc ggaaggtgca tgctggaagc tctgtataag gagcctcgga aggtgcatgc    2400
tggaagctct gtataaggag cctcggaagg tgcatgctgg aagctctgta taaggagcct    2460
cggaaggtgc atgctggaag ctctgtataa ggagcctcgg aaggtgcatg ctggaagctc    2520
tgtataagga gcctcggaag gtgcatgctg gaagctctgt ataaggagcc tcggaaggtg    2580
catgctggaa gctctgtata aggagcctcg gaaggtgcat gctggaagct ctgtataagg    2640
agcctcggaa ggtgcatgct ggaagctctg tataaggagc tcggaaggt gcatgctgga    2700 agctctgtat aaggagcctc ggaaggtgca tgctggaagc tctgtataag gagcctcgga    2760
aggtgcatgc tggaagctct gtataaggag cctcggaagg tgcatgctgg aagctctgta    2820
taaggagcct cggaaggtgc atgctggaag ctctgtataa ggagccttgg aaggtgcatg    2880
ctggaagctc tgtataagga gccttggaag gtgcatgctg gaagctctgt ataaggagcc    2940
ttggaaggtg catgctggaa gctctgtata aggagccttg ga                      2982
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 10
gctctgtata aggagcctcg g          21

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 11
gctctgtata aggagcctcg gaaggtgcat gctggaa                                    37

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttccagcatg cacctt                                                          16

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctctgtata aggagcctcg gaaggtgcat gctggaagct ctgtataagg agcctcggaa           60
ggtgcatgct ggaag                                                           75

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctctgtata aggagccttg gaaggtgcat gctggaa                                    37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctctgtata aggagccttg gaaggtgtat gctggaa                                    37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gctctgtata aggagcctct taaggtgcac gttgtaa                                    37

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
ctctgtataa ggagcctcgg aaggtgcatg ctggaag                              37

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gactctgtat aaggagcctc ggaaggtgca tgctgga                              37
```

CELL-BASED GENOMIC RECORDED ACCUMULATIVE MEMORY

RELATED APPLICATIONS

This application claims the benefit of U.S. provisional patent application Ser. No. 61/901,418, filed on Nov. 7, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 19, 2015, is named 4194.3002US1_SL.txt and is 10,143 bytes in size.

BACKGROUND

Currently there is great interest in data sensing devices capable of measuring a signal and recording what is measured. A standard approach to creating such sensor devices is the use of semiconductor based electronics in which both the sensor and memory are comprised of transistor based integrated circuits. Although such devices can be made small relative to human dimensions, they are limited in the ultimate size reduction which can be achieved by the size limits to which transistor logic can be scaled (current lithographic design rules are ~18 nm corresponding to transistor sizes or memory bit sizes of ~$100^3$ $nm^3$) thus limiting them from a wide range of applications on the nanoscale such as recording information inside of a cell. Additional shortcomings of electronic circuits is that they generally operate far from the physical limits of energy consumption and represent a manufactured artifact, limiting the ultimate cost which can be achieved of such devices and thus limiting their use in applications where large number of sensors are needed such as monitoring large areas of water or land (e.g. 100's of sq. km.) with high densities of sensors.

In distinction to electronics, the molecular elements of living cells, particularly DNA and proteins, possess a number of attributes which make them compelling for sensing and data recording. The 4 nucleotides of DNA, Guanine (G), Adenine (A), Thymine (T) and Cytosine (C) each represent 2 bits of information and in double stranded form have a volume of ~$0.34^3$ $nm^3$ representing a volumetric bit density about 25 million greater than that of the current state of the art electronic memory. In addition, proteins and protein switches serve as highly selective sensor elements and cells operate at close to physical limits for energy consumption.

It would be desirable to design and use a cell based system for sensing and recording data from the cellular environment and for reading and measuring the recorded data.

SUMMARY

A cell-based genomic Recorded Accumulative Memory (geRAM) system (also referred to herein as Genomically Encoded Memory (GEM)), is described, in which data from cell based (molecular) sensors is recorded in the genome or plasmid of a biological cell. GeRAM is also referred to herein as a recombinant cell-based data sensing and recording system.

The cell-based data sensing and recording system of the invention comprises at least one nucleic acid sequence encoding at least one directed endonuclease specific to at least one target sequence located within the cell wherein the at least one directed endonuclease is operably linked to at least one inducible promoter, wherein the at least one inducible promoter is induced by at least one signal originating from outside of the cell, and wherein upon inducement of the promoter in response to the signal, the promoter causes expression of the directed endonuclease wherein the expressed directed endonuclease binds to, and cuts the target sequence located within the cell, wherein the cell is capable of repairing the cut in the target sequence and wherein the repair of the target sequence introduces at least one error in the target sequence, wherein the presence of the at least one error in the target sequence provides a data record that the cell was exposed to the at least one signal originating from outside the cell.

The cell based data sensing and recording systems of the invention may be used in methods for detecting changes in a nucleic acid sequence in a cell in response to a physical and/or chemical signal [of interest] originating outside or inside of the cell. This process also is referred to herein as sensing and recording data from the cellular environment in a cell. The cell based data sensing and recording systems of the invention may be used in methods for determining the presence of and/or the level of at least one signal of interest originating outside or inside of a cell.

BRIEF DESCRIPTION OF THE DRAWINGS

Other aspects, advantages and novel features of the invention will become more apparent from the following detailed description of the invention when considered in conjunction with the accompanying drawings wherein:

FIG. 1A through FIG. 1E are schematic representations of the CRISPR/Cas9 system used to recognize a genomic recognition site, cut the recognition site followed by error prone Non-Homologous End-Joining (NHEJ) leaving a signature of the cutting event. Figures disclose SEQ ID NOS 1-2, 1, and 3-6, respectively, in order of appearance.

FIG. 6 shows *E. coli* colonies illuminated with UV lamp showing increased loss of fluorescence with longer exposure to arabinose that induces guide RNA.

FIG. 9 shows the nucleic acid sequence (SEQ ID NO: 9) of a tandem repeat with a selected recognition sequence occurring in 81 repeats of 37 bps on MM9 Chr 7.

FIG. 13 is a schematic representation of an Algorithm for calling indels on sequencing read out. Figure discloses SEQ ID NOS 13, 11, and 14-18, respectively, in order of appearance.

DETAILED DESCRIPTION

Figures 1C, 1D, 1E:
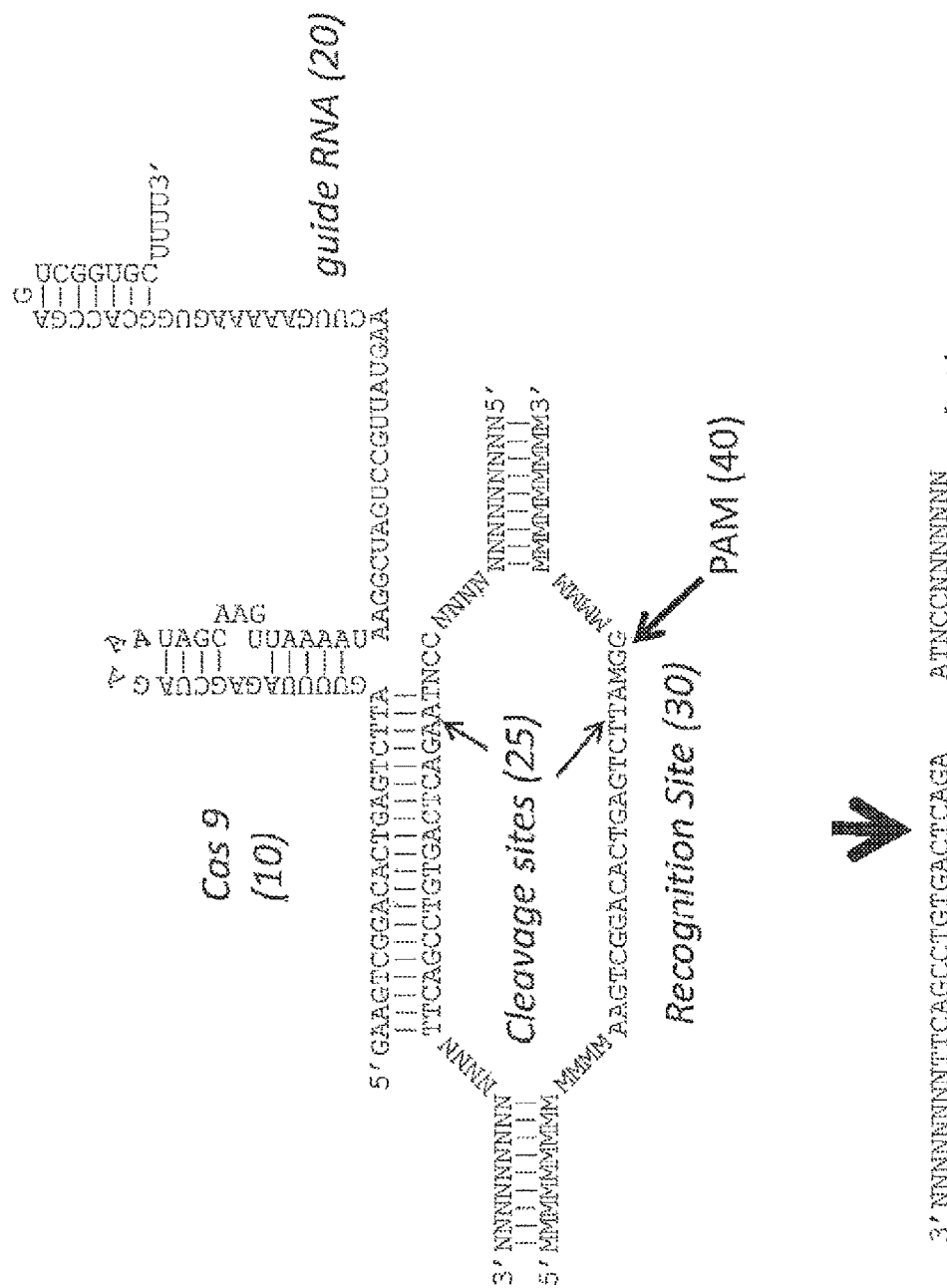

The present invention relates to a cell based genomic Recorded Accumulative Memory (geRAM) system (also referred to herein as Genomically Encoded Memory (GEM)) for recoding data (i.e., changes in nucleic acid sequences in cellular DNA in response to physical and/or chemical signal(s)) from the cellular environment. GeRAM, or GEM, may also be referred to herein as a "cell-based data sensing and recording system". Specifically, the invention provides the encoding of data into endogenous recognition sites or, alternatively, exogenous recognition sites that have been inserted into a genome of a cell or on a plasmid within the cell. This data can be propagated through cell lineages by replication and read through DNA sequencing.

The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, lentiviruses, replicative defective lentiviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Plasmids suitable for expressing embodiments of the present invention, methods for inserting nucleic acid sequences into a plasmid, and methods for delivering recombinant plasmids to cells of interest are known in the art.

Several aspects of the invention relate to vector systems comprising one or more vectors, or vectors as such. Vectors can be designed for expression of transcripts (e.g. nucleic acid transcripts, proteins, or enzymes) in prokaryotic or eukaryotic cells. For example, transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press. San Diego, Calif. (1990). Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). Expression of proteins in prokaryotes is most often carried out in *Escherichia coli* with vectors containing constitutive or inducible promoters directing the expression of proteins. Examples of suitable inducible *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. *Gene* 54:

113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Appropriate DNA segments may be inserted into a vector by a variety of procedures. In general, DNA sequences may be inserted into an appropriate restriction endonuclease site(s) by procedures known in the art, which may be performed without undue experimentation by a skilled artisan. A DNA segment in an expression vector may be operatively linked to an appropriate expression control sequence(s) (i.e., a promoter) to direct synthesis. Such promoters may include any promoter known in the art for expression either in vivo or in vitro. Promoters which may be used in embodiments of the present invention may include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). The promoters which may be used in embodiments of the present invention may also be inducible, such that expression may be decreased or enhanced or turned "on" or "off". For example, promoters which respond to a particular signal (e.g., small molecule, metabolite, protein, molecular modification, ion concentration change, electric charge change, action potential, radiation, UV, and light) may also be used. Additionally, a tetracycline-regulatable system employing any promoter such as, but not limited to, the U6 promoter or the H1 promoter, may be used. By way of example and not of limitation, promoters which respond to a particular stimulus may include, e.g., heat shock protein promoters, and Tet-off and Tet-on promoters.

"Operably linked" is intended to mean that the nucleotide sequence of interest is linked to the promoter in a manner that allows or enhances the expression of the nucleotide sequence (e.g. in an in vitro transcription/translation system or in a host cell when the vector is introduced into the host cell).

The term "guide RNA" refers to a polynucleotide sequence comprising a guide sequence. The term "guide sequence" refers to the about 20 bp sequence within the guide RNA that specifies the target site and may be used interchangeably with the terms "guide" or "spacer". In some embodiments, the guide sequence is at least 15, 16, 17, 18, 19, 20, 25 nucleotides, or between 10-30, or between 15-25, or between 15-20 nucleotides in length. A guide sequence is any polynucleotide sequence having sufficient complementarity with a target polynucleotide sequence to hybridize with the target sequence and direct sequence-specific binding of a directed endonuclease to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. A guide sequence may be selected to target any target sequence.

"Target sequence" or "recognition sequence" or "recognition site" are used interchangeable herein and refer to a polynucleotide of a particular sequence to which a guide sequence is designed to have complementarity, where hybridization between a target sequence and a guide sequence promotes the formation of directed endonuclease complex. Full complementarity is not necessarily required, provided there is sufficient complementarity to cause hybridization. The target sequence can be any polynucleotide endogenous or exogenous to the cell. For example, the target sequence can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). A recognition site or recognition sequence can be an engineered or synthetic DNA polynucleotide that has been inserted into the genome of a cell or on a plasmid within the cell or, alternatively, inter-genic or intron regions which include, but are not limited to, tandem repeats or distributed repeats, short interspersed repetitive elements (SINEs) or long interspersed repetitive elements (LINEs).

"Targeting" or "targeted" means the process of design and selection of a gRNA that will specifically hybridize to a target recognition site and induce a desired effect.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%/, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay". Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides a recombinant cell-based data sensing and recording system comprising a cell comprising at least one nucleic acid sequence encoding at least one directed endonuclease specific to at least one target sequence located within the cell wherein the at least one directed endonuclease is operably linked to at least one inducible promoter, wherein the at least one inducible promoter is responsive to at least one signal of interest originating from outside or inside of the cell, and wherein upon inducement of the promoter in response to the signal, the promoter causes expression of the directed endonuclease wherein the expressed directed endonuclease binds to, and cuts or nicks the target sequence located within the cell, wherein the cell is capable of repairing the cut or nick in the target sequence and wherein the repair of the target sequence introduces at least one error (also referred to herein as "indels") such as, but not limited to, an insertion, deletion, or substitution of one or more nucleotides in the target sequence, wherein the presence of the at least one error in the target sequence provides a data record that the cell was exposed to the at least one signal originating from outside or inside the cell.

The cell based data sensing and recording systems of the invention may be used in methods for detecting changes in a nucleic acid sequence in a cell in response to a physical and/or chemical signal [of interest] originating outside or inside of the cell. This process also is referred to herein as sensing and recording data from the cellular environment in a cell. The cell based data sensing and recording systems of the invention may be used in methods for determining the presence of and/or the level of at least one signal of interest originating outside or inside of a cell. In some embodiments, the methods comprise providing a recombinant cell-based data sensing and recording system comprising a cell comprising at least one nucleic acid sequence encoding at least one directed endonuclease specific to at least one target sequence located within the cell wherein the at least one directed endonuclease is operably linked to at least one inducible promoter, wherein the at least one inducible promoter is induced by at least one signal [of interest] originating from outside or inside of the cell, and wherein upon inducement of the promoter in response to the signal, the promoter causes expression of the directed endonuclease wherein the expressed directed endonuclease binds to, and cuts or nicks the target sequence located within the cell, wherein the cell is capable of repairing the cut or nick in the target sequence and wherein the repair of the target sequence introduces at least one error (also referred to herein as "indels") such as, but not limited to, an insertion, deletion, or substitution of one or more nucleotides in the target sequence, harvesting the cell or the cell's progeny; isolating the DNA from the cell or the cell's progeny; sequencing the target site(s) within the DNA; and comparing the sequenced target site with a reference DNA sequence, wherein the introduction of an error into the target sequence of the cell or its progeny is indicative of the presence of the signal.

In some embodiments, the cell based data sensing and recording systems of the invention may be used in methods for monitoring the activation of all known signaling pathways. Additionally, since most of the cellular phenotypic changes are communicated through transcriptional changes, the use of transcription as the counter input will facilitate detection of subtle cellular reactions to different treatments or experimental conditions. Therefore, the counter will be designed as an inducible guide RNA under the regulation of a promoter of interest. In addition to recording levels of transcriptional activation, the proposed synthetic biological circuit can provide a compact barcode for determining cell lineage of proliferating cells and serve as a platform for more complex computational operations in the mammalian cell.

As used herein, the at least one signal of interest originating from outside or inside of the cell refers to any physical or chemical signal including, but not limited to, small molecule, metabolite, protein, molecular modification, ion concentration change, electric charge change, action potential, radiation, UV, and light.

The cell is capable of repairing the cut or nicked target sequence by, for example, native end joining mechanisms. Native end joining mechanisms include, but are not limited to, Non-Homologous End Joining (NHEJ) or Alternative End Joining (AEJ). These repair mechanisms have a finite probability of introducing an error and modify a recognition sequence in a way that prevents future localization of the directed endonuclease. As such, these error(s) represent a record of the data and can serve as a counting currency the readout of which will be sequence based.

Any directed endonuclease known to those skilled in the art including, but are not limited to, Zinc Finger Nucleases (ZFNs), Transcription Activator Like Effector Nucleases (TALENs), and the Clustered Regularly Interspaced Palindromic Repeats (CRISPR) system. In general, "CRISPR system" refers collectively to transcripts and other elements involved in the expression of or directing the activity of CRISPR-associated ("Cas") genes. Directed endonucleases can be designed to target specific recognition sites. This programmable specificity allows the library of available recognition sequences to grow exponentially with the length and/or number of the recognition sequence(s). As discussed further below, scalable memory follows from the large number of different recognition sequences and is achieved by the indel a directed endonuclease can leave on its recognition sequence.

In some embodiments, the recombinant cell-based data sensing and recording system comprises a cell comprising a vector system comprising one or more vectors, wherein the one or more vectors drive the inducible expression of the directed endonuclease. In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site downstream of a promoter. In a preferred embodiment the promoter is an inducible promoter. In some embodiments, a vector comprises two or more insertion sites so as to allow insertion of a directed endonuclease at each site. In such an arrangement, the two or more directed endonucleases may comprise two or more copies of a single directed endonuclease, two or more different directed endonucleases, or combinations of these. In such an arrangement, the two or more directed endonucleases may be operably linked to the same promoter or to different promoters. In a preferred embodiment, the two or more directed endonucleases may be operably linked to different inducible promoters wherein each inducible promoter is responsive to a different physical and/or chemical signal.

In a preferred embodiment, the vector system comprises one or more vectors that drive expression of the components of the CRISPR system. In some embodiments, an inducible promoter is operably linked to one or more elements of a CRISPR system so as to drive expression of the one or more elements of the CRISPR system. In some embodiments, the system comprises: (a) at least one first promoter operably linked one or more guide RNAs; and (b) at least one second promoter operably linked to a nucleic acid sequence encoding a CRISPR enzyme, provided that at least one of the first promoter or the second promoter is an inducible promoter. In some embodiments, a vector comprises one or more insertion sites (e.g. about or more than about 1, 2, 3, 4, 5, 6, 7, 8, 9, 10, or more insertion sites) downstream of a promoter. In some embodiments, a vector comprises two or more insertion sites so as to allow insertion of a guide RNA at each site. In such an arrangement, the two or more guide RNAs may comprise two or more copies of a single guide RNA, two or more different guide RNAs, or combinations of these. In such an arrangement, the two or more guide RNAs may be operably linked to the same promoter or to different promoters. In a preferred embodiment, the two or more guide RNAs may be operably linked to different inducible promoters wherein each inducible promoter is responsive to a different physical and/or chemical signal. Without wishing to be bound to any particular theory, when the guide RNA and the CRISPR enzyme are expressed, the guide RNA directs sequence-specific binding of a CRISPR complex to a target sequence in the cell, wherein the CRISPR complex comprises a CRISPR enzyme complexed with the guide RNA.

In some embodiments, components (a) and (b) are located on the same or different vectors of the system. In a preferred embodiment components (a) and (b) are located on the same vector. In a preferred embodiment components (a) and (b) are located on different vectors. In some embodiments, component (a) further comprises two or more guide RNAs operably linked to the at least one first promoter, wherein when expressed, each of the two or more guide RNAs direct sequence specific binding of a CRISPR complex to a different target sequence in the cell. In some embodiments, component (a) further comprises two or more guide RNAs operably linked to different promoters, wherein when expressed, each of the two or more guide RNAs independently direct sequence specific binding of a CRISPR complex to a different target sequence in the cell. In such an arrangement, the two or more different promoters are preferably inducible promoters responsive to different physical and/or chemical signals. In some embodiments, component (b) further comprises two or more CRISPER enzyme coding sequences operably linked to different promoters, wherein when expressed, each of the CRISPER enzymes are complexed with a guide RNA of component (a) which direct sequence specific binding of a CRISPR complex to a target sequence in the cell. In such an arrangement, the two or more different promoters are preferably inducible promoters responsive to different physical and/or chemical signals.

In one aspect, the invention provides a recombinant cell-based data sensing and recording system comprising a cell comprising (a) at least one first promoter operably linked to one or more guide RNAs; and (b) at least one second promoter operably linked to an nucleic acid sequence encoding a CRISPR enzyme. In some embodiments, the host cell comprises components (a) and (b). In some embodiments, component (a), component (b), or components (a) and (b) are part of a vector system transiently transfected into the host cell. In a preferred embodiment, component (a), component (b), or components (a) and (b) are stably integrated into a genome of the host cell. In some embodiments, component (a) further comprises two or more guide RNAs operably linked to the at least one first promoter, wherein when expressed, each of the two or more guide RNAs direct sequence specific binding of a CRISPR complex to a different target sequence in the cell. In some embodiments, component (a) further comprises two or more guide RNAs operably linked to different promoters, wherein when expressed, each of the two or more guide RNAs direct sequence specific binding of a CRISPR complex to a different target sequence in the cell. In such an arrangement, the two or more different promoters are preferably inducible promoters responsive to different physical and/or chemical signals. In some embodiments, component (b) further comprises two or more CRISPER enzyme coding sequences operably linked to different promoters, wherein when expressed, each of the CRISPER enzymes are complexed with a guide RNA of component (a) which direct sequence specific binding of a CRISPR complex to a target sequence in the cell. In such an arrangement, the two or more different promoters are preferably inducible promoters responsive to different physical and/or chemical signals.

When multiple different guide RNAs are used, a single vector may be used to target CRISPR activity to multiple different, corresponding target sequences within a cell. Alternatively, when multiple different guide RNAs are used, multiple vectors may be used to target CRISPR activity to multiple different, corresponding target sequences within a cell. For example, a single vector, or multiple vectors, may comprise about or more than about 1, 2, 3, 4, 5, 6, 7, 8, 9, 10, 15, 20, or more guide RNAs. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a promoter operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3. Csf4, homologs thereof, or modified versions thereof.

In some embodiments, a vector comprises two or more insertion sites so as to allow insertion of an enzyme-coding sequence encoding a CRISPR enzyme at each site. In such an arrangement, the two or more enzyme-coding sequences may comprise two or more copies of a single enzyme-coding sequence, two or more different enzyme-coding sequences, or combinations of these. In such an arrangement, the two or more enzyme-coding sequences may be operably linked to different promoters in a single vector or in multiple vectors. For example, a single vector, or multiple vectors, may comprise about or more than about 1, 2, 3, 4, 5, 6, 7, 8, 9, 10, 15, 20, or more enzyme-coding sequences. In some embodiments, about or more than about 1, 2, 3, 4, 5, 6, 7, 8, 9, 10, or more such enzyme-coding sequence-containing vectors may be provided, and optionally delivered to a cell.

Typically, in the context of an endogenous CRISPR system, formation of a CRISPR complex results in cleavage (e.g., a cutting or nicking) of one or both strands in or near (e.g. within 1, 2, 3, 4, 5, 6, 7, 8, 9, 10, 20, 50, or more base pairs from) the target sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme and a guide RNA are operably linked to separate promoters on separate vectors. Alternatively, a Cas enzyme and a guide RNA are operably linked to separate promoters in a single vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction.

In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9a nickase include, without limitation, H840A, N854A, and N863A. In some embodiments, a Cas9 nickase may be used in combination with guide RNA(s), e.g., two guide RNAs, which target respectively sense and antisense strands of the DNA target. This combination allows both strands to be nicked and used to induce NHEJ.

In another embodiment of this aspect, the directed endonuclease is ZFN or TALEN. Zinc Fingers (ZFs) and Transcription Activator Like Effectors (TALEs) are proteins with peptide sequences designed as a succession of fused protein domains that each contribute recognition to a subsequence of the overall DNA recognition sequence.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a CRISPR enzyme in combination with (and optionally complexed with) a guide RNA is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Cell lines are available from a variety of sources known to those with skill in the art (see, e.g., the American Type Culture Collection (ATCC) (Manassus, Va.)). In some embodiments, a cell transfected with one or more vectors described herein is used to establish a new cell line comprising one or more vector-derived sequences. In some embodiments, a cell transiently transfected with the components of the system as described herein (such as by transient transfection of one or more vectors) is used to establish a new cell line. In some embodiments, cells transiently or non-transiently transfected with one or more vectors described herein, or cell lines derived from such cells are used in assessing one or more test compounds.

In an aspect, cells and cell lines comprising one or more vectors of the invention are provided. Suitable cells include, but are not limited to, mammalian cells (e.g., mouse cells, human cells, rat cells, etc.), primary cells, stem cells, avian cells, plant cells, insect cells, bacterial cells, fungal cells (e.g., yeast cells), and any other type of cell known to those skilled in the art.

In an aspect the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In some embodiments, said vectors are delivered to the cell in a subject. In some embodiments, said modifying takes place in said cell in a cell culture. In some embodiments, the method further comprises isolating said cell from a subject prior to said modifying. In some embodiments, the method further comprises returning said cell and/or cells derived therefrom to said subject.

The presence of and/or degree of exposure to the physical and/or chemical signal(s) can be determined by a comparison of the sequence of the target recognition site to a reference genome or plasmid. This geRAM data can be read through sequencing of the target recognition sites.

To assay for an induced error in the target sequenced, nucleic acid contained in a sample is first extracted according to standard methods in the art. For instance, DNA can be isolated using various lytic enzymes or chemical solutions according to the procedures set forth in Sambrook et al. (1989), or extracted by nucleic-acid-binding resins following the accompanying instructions provided by the manufacturers. The DNA contained in the extracted nucleic acid sample is then detected by amplification procedures or conventional hybridization assays (e.g. Southern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In one aspect, the invention provides kits containing any one or more of the elements disclosed in the above methods and compositions. In some embodiments, the kit comprises a vector system and instructions for using the kit. In some embodiments, the vector system comprises (a) at least one first promoter operably linked to one or more guide RNAs; and (b) at least one second promoter operably linked to a nucleic acid sequence encoding a CRISPR enzyme. Elements may be provide individually or in combinations, and may be provided in any suitable container, such as a vial, a bottle, or a tube. In some embodiments, the kit includes instructions in one or more languages, for example in more than one language.

Single Channel Cutting. In a preferred embodiment of the invention, data is encoded into the cell by means of signal (e.g. small molecule, metabolite, protein, light) induced targeted double stranded cutting of recognition sites in the genome which are repaired by a repair mechanism (e.g. NHEJ—Non-homologous end joining) which has a finite probability of inducing an error upon repair of the junction break. Data is read out by sequencing the recognition sites in the genome and comparing it to a reference (uncut) genome to infer the degree of exposure to the inducing signal. Induced targeted cutting of recognition sites may be carried out by signal induced expression of sequence specific DNA recognition systems including Zn Finger nucleases, TALENs (Transcription activator-like effector nucleases) and the CRISPR (Clustered Regularly Interspaced Short Palindromic Repeats) system.

Single Channel—Nicking. In a further preferred embodiment of the invention, data is encoded into the cell by means of signal (e.g. small molecule, metabolite, protein, light) induced targeted nicking of recognition sites in the genome which are repaired by a repair mechanism (e.g. nick repair) which has a finite probability of inducing an error upon repair of the nick. Data is read out by sequencing the recognition sites in the genome and comparing it to a reference (un-nicked) genome to infer the degree of exposure to the inducing signal. Induced targeted nicking of recognition sites may be carried out by signal induced expression of sequence specific DNA recognition systems including Zn Finger nucleases, TALENs (Transcription activator-like effector nucleases) and the CRISPR (Clustered Regularly).

Multi-Channel Cutting. In another preferred embodiment of the invention, data from a plurality of signals (e.g. small molecule, metabolite, protein, light) is simultaneously encoded by means of signal induced targeted cutting or nicking of multiple recognition sites in which each signal induces the cutting of a separate recognition site. Recognition site cuts or nicks are repaired with a finite error rate thus comprising a record of the signal when compared to the original uncut sequence. Data is read out by sequencing the recognition sites in the genome and comparing it to a reference (uncut) genome to infer the degree of exposure to the inducing signals.

Dynamic Memory and Circuits. In another preferred embodiment of the invention a dynamic (self-sustaining) memory is implemented by signal induced expression of a gene which codes for a sequence specific recognition element which activates itself. An example of such a system is the signal induced expression of a gRNA which recognizes and activates its own promoter thus preserving a memory of the exposure of the cell to the initial inducing signal.

In a second aspect of this preferred embodiment a counter circuit is implemented by means of dynamic memory.

Additional applications are possible if one obtains single cell sequence data from an ensemble of such cells including time stamping of data (i.e. the time profile of a signal) as well as the ability to track cell lineage.

FIGS. 1*a* through 1*e* show schematic representations of the CRISPR/Cas9 system which constitutes a key element of a preferred embodiment of a genomically encoded memory. Referring to FIG. 1(*a*) the Cas9 protein (10) is complexed to a guide RNA (gRNA 20) which has been designed to be complimentary to a double stranded DNA recognition site (FIG. 1*b*—30) which in a preferred embodiment is part of the non-coding part of a host organism genome.

As is known in the art (B. Wiedenheft, S. H. Sternberg, J. A. Doudna, Nature 482, 331 (2012); D. Bhaya, M. Davison, R. Barrangou, Annu Rev. Genet. 45, 273 (2011); M. P. Terns, R. M. Terns, Curr. Opin. Microbiol. 14, 321 (2011); M. Jinek et al., Science 337, 816 (2012).), referring to FIG. 1(*c*) the Cas9 (10) protein possess a helicase activity which dehybridizes the recognition site (30) into single stranded regions to which the gRNA (20) can hybridize. Referring to FIG. 1(*d*) the Cas9 (10)+gRNA (2) complex then cleaves the recognition site (30) at cleavage sites (25) which are 5 nucleotide bases in from the PAM (Protospacer Adjacent Motif) site (40) of the recognition site forming a double stranded break. Referring to FIG. 1(*e*) this double stranded break may then be repaired by non-homologous end joining (NHEJ) which has a finite probability (Reference: Mali, Prashant, et al. "RNA-guided human genome engineering via Cas9." Science 339.6121 (2013): 823-826.—Supplemental material) of inducing a sequence error which serves as a record that a double stranded break has occurred.

This mechanism of DNA site recognition, followed by cutting and error prone repair may now form the basis of an intracellular memory.

Figure 2:
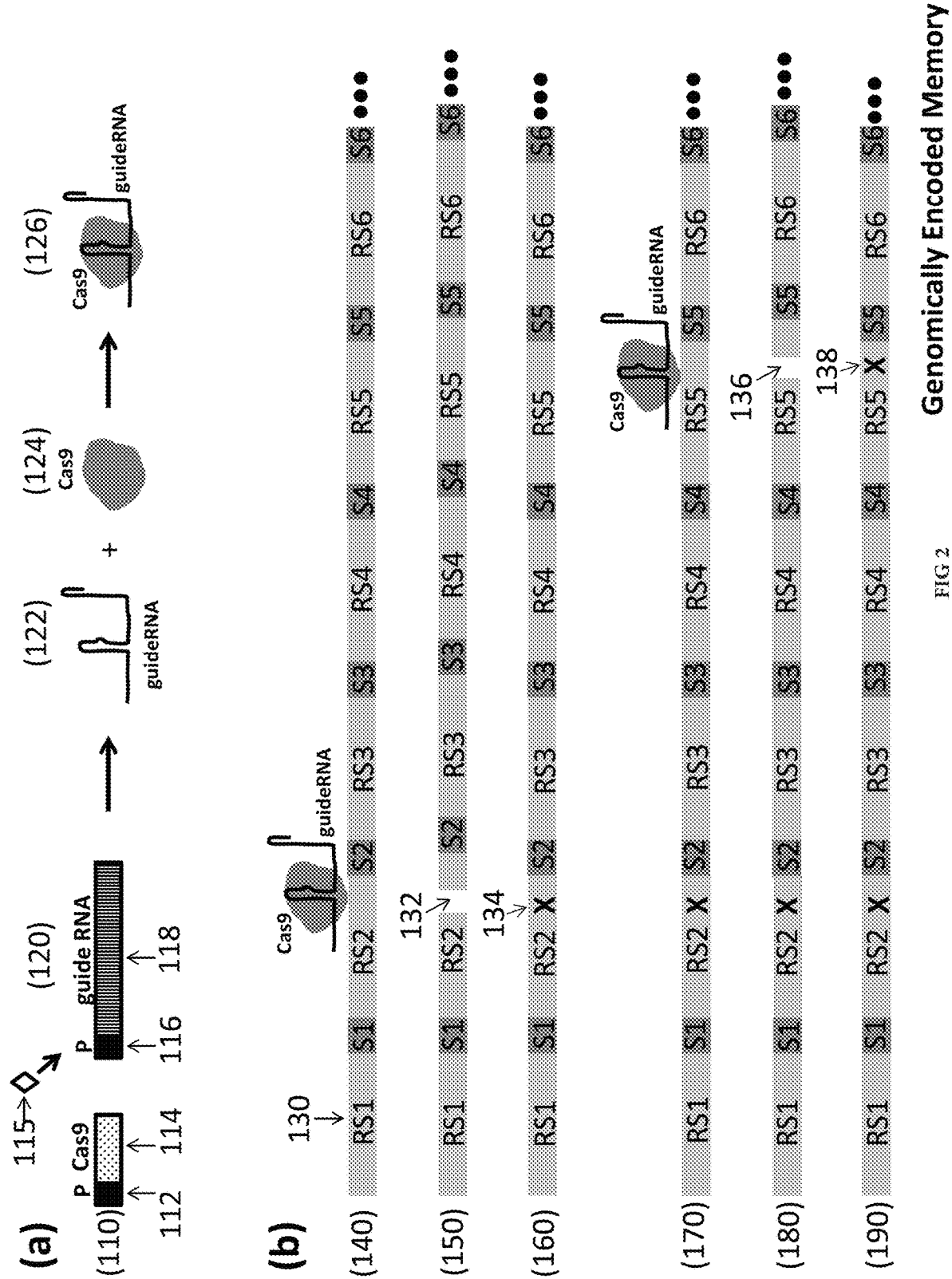
FIG. 2 is a schematic Representation of a single channel Genomically Encoded Memory based on Clustered Regularly Interspaced Short Palindromic Repeats (CRISPR).

Referring to FIG. 2, a single channel version of a preferred embodiment of the genomically encoded memory invention is schematically shown. Referring to FIG. 2(a) a first gene coding region (110) comprising a promoter p (112) and the gene encoding the protein Cas9 (114) is arranged to constituently express the protein Cas9 (124). A second coding region (120) comprising an inducible promoter (116) and the DNA sequence coding for a specific guide RNA (118) designed to target a recognition site (e.g. RS1, RS2 etc. in FIG. 2(b)) is arranged to express the gRNA (122) when said coding region (120) is induced by inducer (115). Inducer (115) may be a small molecule, secondary metabolite, peptide, protein, light, temperature or any other endogenous or exogenous signal which can initiate the transcription of a gRNA.

Referring to FIG. 2(b) a plurality of recognition sites (RS1, RS2 . . . 130) and spacers (S1,S2 . . . ) comprise a memory scratch pad (140) which can record events which take place in the cell which can later be read out by sequencing. This memory scratch pad may be synthetic, comprising a non-natural or heterologous sequence of repeats or alternatively may comprise a natural, non-essential (e.g. non-coding or inter-genic) sequence which may be a tandem repeat or may be a distributed repeat (e.g. short interspersed repetitive elements (SINE) or long interspersed repetitive elements (LINE)).

The operation of the Genomically Encoded Memory (GEM) is as follows. When an inducer (115) (e.g. small molecule, metabolite, peptide, protein, light, temperature) is present it activates the production of gRNA (122) which has been designed to be complimentary to recognition sites (130) (RS1, RS2, RS3 . . . ) which complexes with constitutively expressed Cas9 (124) to form a gRNA+Cas9 Complex (126). This complex (126) in turn binds at random with recognitions sites (130) (RS1, RS2, RS3) in the memory scratch pad (140). As described in FIG. 1, this binding induces a double stranded break (132) in the memory scratch pad to result in a cut memory scratch pad (150). Finally the cut in the memory scratch pad may be repaired with non-homologous end joining (NHEJ). With a finite probability this NHEJ repair will contain a sequence error (134) representing a permanent record (160) of the cutting event which is a measure of the level of induction of the gRNA thus recording information about the level of inducer (115) present. If the presence of the inducer persists over time, then additional data points (138) may be recorded at other recognition sites (170, 180, 190) resulting in a final record (190) representing total or accumulated inducer exposure. The final data transcript may be read out by sequencing. In a preferred embodiment sequencing may be carried out by next generation sequencing. If the spacer sequences are unique they form a bar code differentiating the repeated recognition site sequences such that the sequencing analysis can differentiate between the different recognitions sites (e.g. RS2, RS5) which have been cut. This in turn imbues a pattern of cut sites which can be used to tag the lineage of a cell line. Alternatively if a sequencing technology with long read length (capable of reading many recognition sites) is used one may also use this to ascertain the pattern of cuts and use this pattern as identifying means to track cell lineage.

An alternative preferred embodiment of the present genomically encoded memory replaces the CRISPR-Cas9 mechanism other another inducible recognition and cutting system which may be Zn Finger nucleases and Tal-E nucleases.

A further alternative preferred embodiment of the present genomically encoded memory replaces the Cas9 mechanism for induced targeted double cutting of DNA, with a mechanism which induces targeted single stranded nicking of DNA such as by the use of Cas9 nickase (Reference: F Ann Ran et al Cell 2013 PMID: 23992846). Here, single stranded nicks are repaired by single stranded nick repair. If the single stranded nick repair has a finite error rate (Mali, Prashant, et al. "RNA-guided human genome engineering via Cas9." Science 339.6121 (2013): 823-826.—Supplemental material) then this represents the recording of a nicking event. A further alternative to single nicking with a single induced gRNA is the use of double nicking Although the typical use of double nicking (Ran, F., et al. "Double nicking by RNA-guided CRISPR Cas9 for enhanced genome editing specificity." Cell (2013).) is where a nick is made in a top strand and then an associated nick is made in the adjacent but offset bottom strand, here a preferred mechanism is in which two nicks are made in the same strand offset by a small number of nucleotide bases. Each nick is made by two different gRNA's. Here each of the two different gRNA's may be induced by the same inducer or by two separate inducers. If the number of bases between two nicks is sufficiently small (<~6 at physiological temperatures) then the small interleaving single stranded oligonucleotide may melt off. During repair this will require that polymerase be used to fill in the gap which will give an increased opportunity for an error to be incorporated thus recording the nicking event.

Such nicking mechanism may be advantageous to the viability of the host organism which generally has an upper limit for the number of simultaneous double stranded cuts which can exist in the genome and still have a viable cell.

An additional alternative preferred embodiment of the present genomically encoded memory invention includes having the memory scratch pad resident on a plasmid within the cell as opposed to within the genome.

Figure 3:
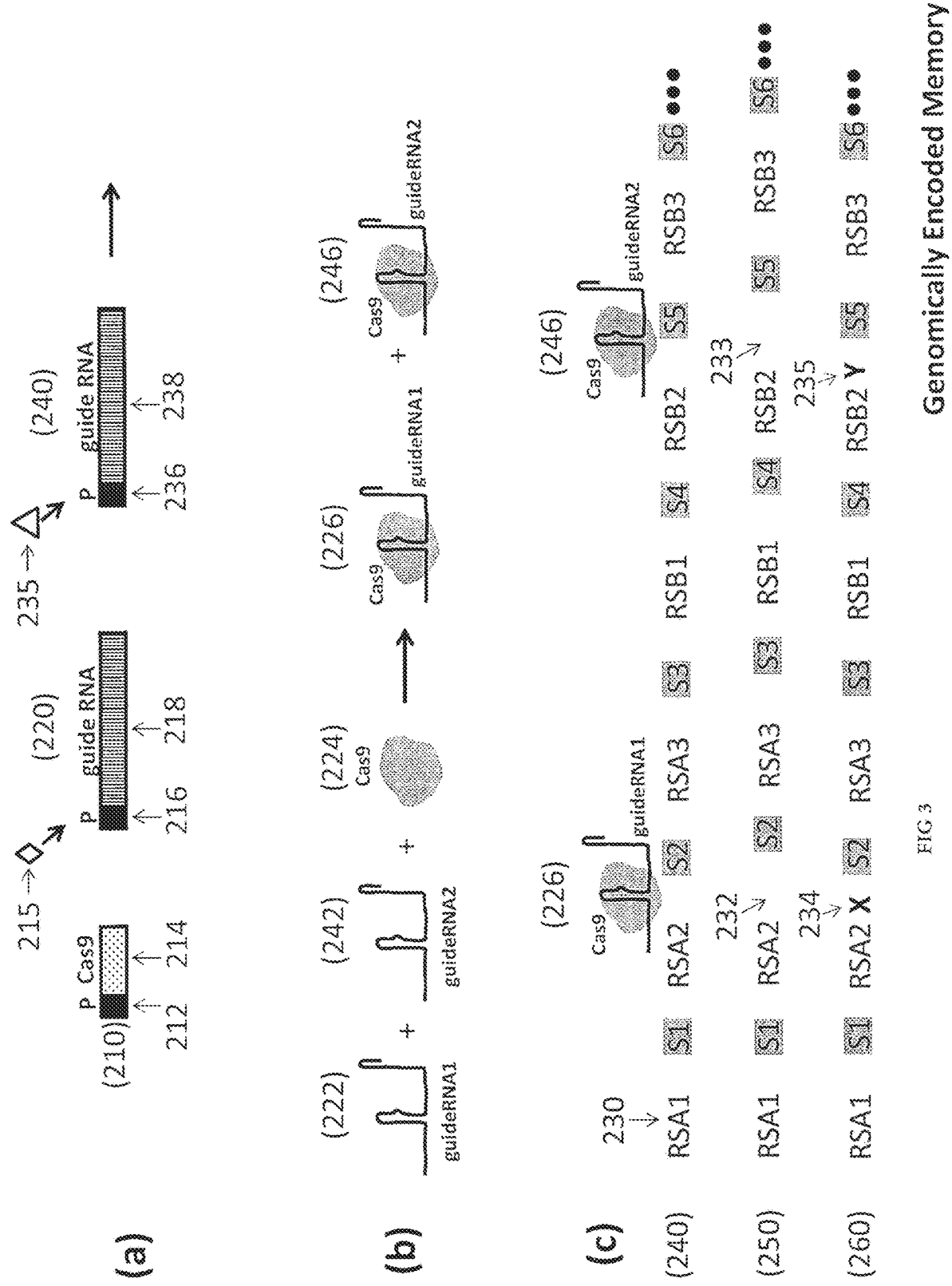
FIG. 3 is a schematic Representation of a multi-channel Genomically Encoded Memory based on Clustered Regularly Interspaced Short Palindromic Repeats (CRISPR).

In addition to a genomically encoded memory which records data from a single inducer (single channel memory) we describe means for recording from multiple inducers in parallel (multichannel memory). Referring to FIG. 3, a multi-channel version of a preferred embodiment of the genomically encoded memory invention is schematically shown. Referring to FIG. 3(a) a first gene coding region (210) comprising a promoter p (212) and the gene encoding the protein Cas9 (214) is arranged to constituently express the protein Cas9 (224). Additional coding regions (220,240) comprising inducible promoters (216,236) and the DNA sequence coding for specific gRNAs (218,238) designed to target separate recognition sites (RSA and RSB in FIG. 3(c) respectively), are arranged to express gRNAs (222,242) when said coding region (220,240) are induced by inducers (215,235) respectively. Inducers (215,235) may be small molecules, secondary metabolites, peptides, proteins, light, temperature or any other signal which can be translated into the transcription of a guideRNA.

Referring to FIG. 3(c), separate guide RNAs (gRNA1 226 and gRNA2 246) target separate recognition sites (RSA and RSB respectively) on the multichannel memory genomic scratchpad DNA sequence (240). As in the case of the single channel memory, induced gRNA expression can lead to double stranded breaks (232,233) or nicks which can lead to DNA repair which has errors (234,235) in the final memory scratch pad (260). The final multichannel memory scratch pad (260) may be read out by sequencing which provides a measure of the total exposure to inducers (215 and 235).

Figure 4:
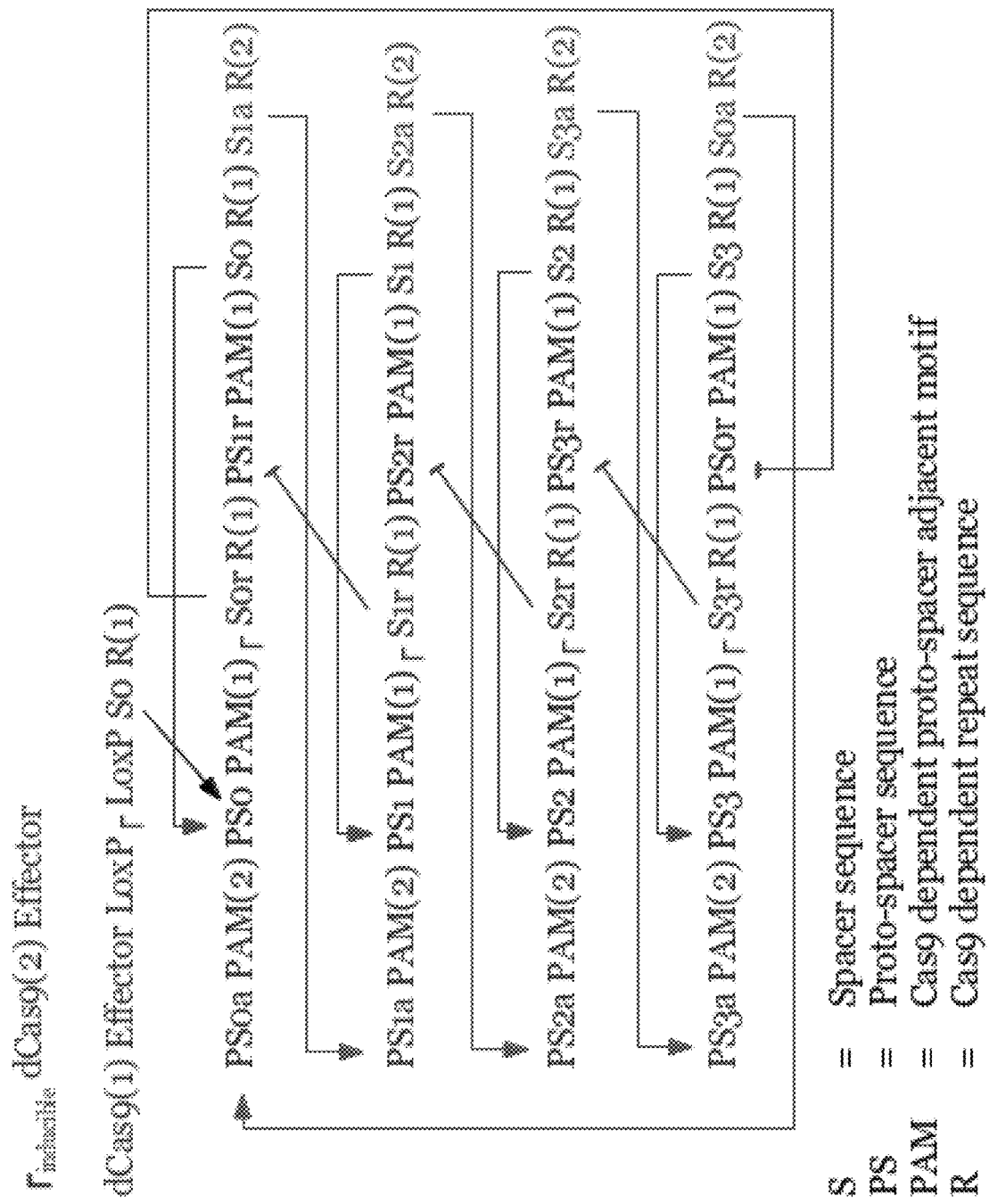
FIG. 4 is a schematic representation of a dynamic cascaded counter induced by light or other induction signal Cascaded counter induced by light or other induction signal. The dynamic modulo-4 counter increments transcriptional state upon each induction. A recombinase (shown with Cre) can be used to initiate and reset the cycle.

Orthogonally active Cas9 enables a dynamic counter that uses one Cas9 fusion to maintain a memory of the state of the counter and orthogonal Cas9 fusions to increment the state of the counter. FIG. 4 shows a schematic representation of a modulo-4 cascaded counter which is clocked (incremented) by light or other induction signal. Application of Cre initiates or resets the counter by flipping the promoter between expression of the first spacer (S) and repeat (R) pair to the expression of an engineered Cas9 that interacts with the transcript of said pair. The state of the counter is preserved with positive feedback on the current expression pattern and negative feedback on the previous expression pattern using spacer and repeat sequences corresponding to this Cas9. An orthogonal Cas9 is either constitutively expressed and complexed with an effector domain upon exposure to light (as shown) or conditionally expressed using an inducible promoter and fused with an effector domain (not shown). Activation or expression of this second Cas9 increments the state using spacer and repeat sequences corresponding to the second Cas9.

The detailed operation of the modulo-4 counter is as follows. Two orthogonal dCas9 ('d' for deactivated cutting domains) are expressed as fusion proteins. dCas9(1) has constitutive expression switched on and off by a recombinase (shown with Cre) and the other dCas9(2) is expressed or activated only upon a signal induction event (e.g. small molecule, metabolite, protein, light, pH etc). When dCas9(1) is not expressed, a guide RNA it complexes with is instead expressed. When dCas9(1) is initially expressed, recent transcripts of such guide RNA initiates the modulo-4 counter by binding to Cas9(1) and the guide RNA's recognition site. This interaction is represented with the black arrow. The position of this recognition site before a weak promoter and linking of dCas9(1) to an effector protein results in the transcription of the "0" state element. Each element transcribes guide RNA that similarly targets a recognition site before the weak promoter of that element. This positive auto-regulation is represented with a blue arrows that loops back on the transcriptional memory state element. Each state element transcribes guide RNA that targets a region right before the weak promoter on the next state element in the sequence. However, this guide RNA only complexes with dCas9(2), which is expressed only upon signal induction. Thus, the the counter increments upon signal induction events. This positive feed-forward interaction is represented by red arrows. Each state element also transcribes guide RNA that targets a region right after the weak promoter on the previous state element in the sequence. This guide RNA complexes with constitutively expressed dCas9(1) and will thereby repress the auto-regulated transcription of the previous state. This negative feedback interaction is represented by the blue bar-ended lines.

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Figure 5:
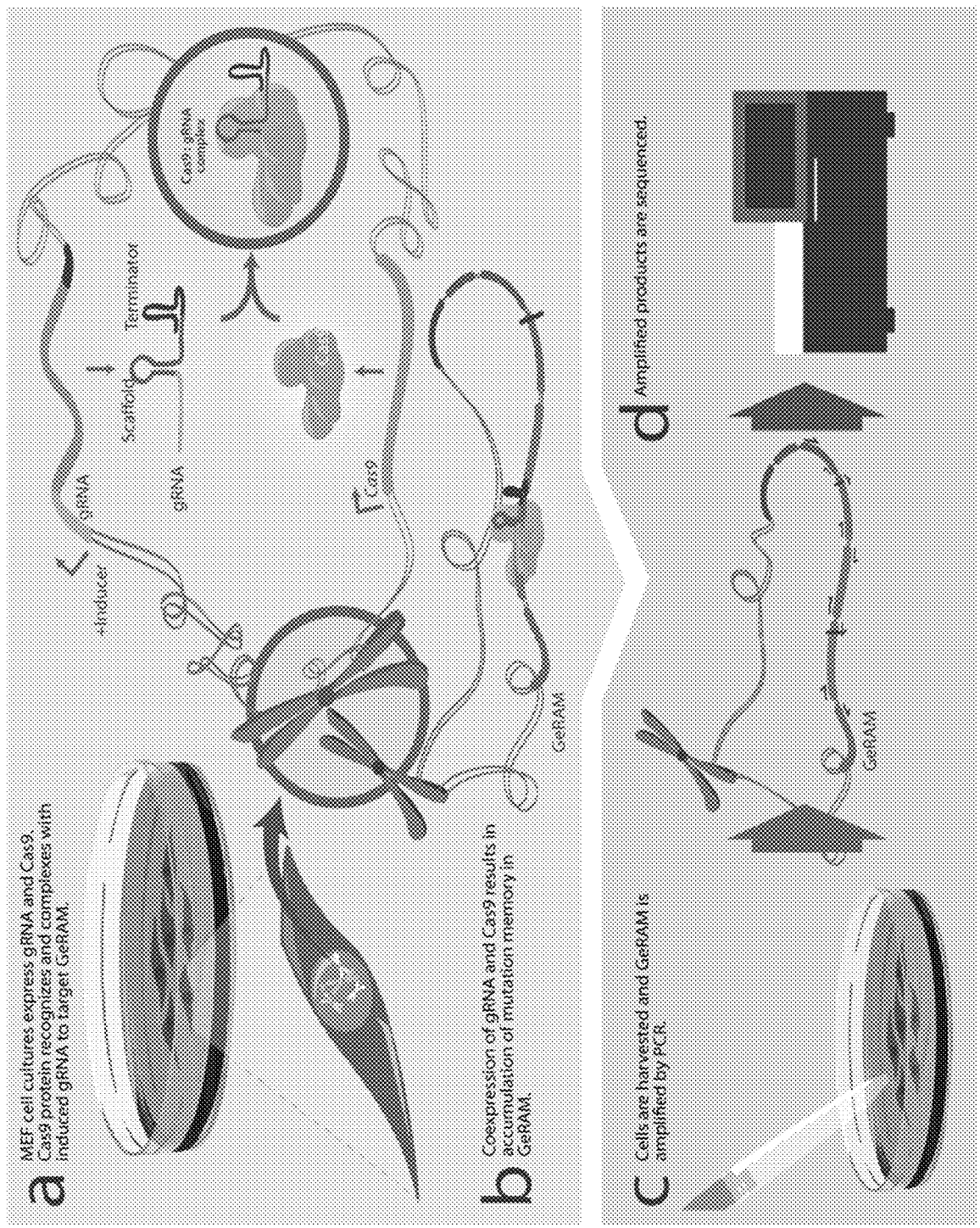
FIG. 5 depicts a workflow diagram for recording information into genomic material with CRISPR/Cas9 and reading out by DNA sequencing.
Figure 7:
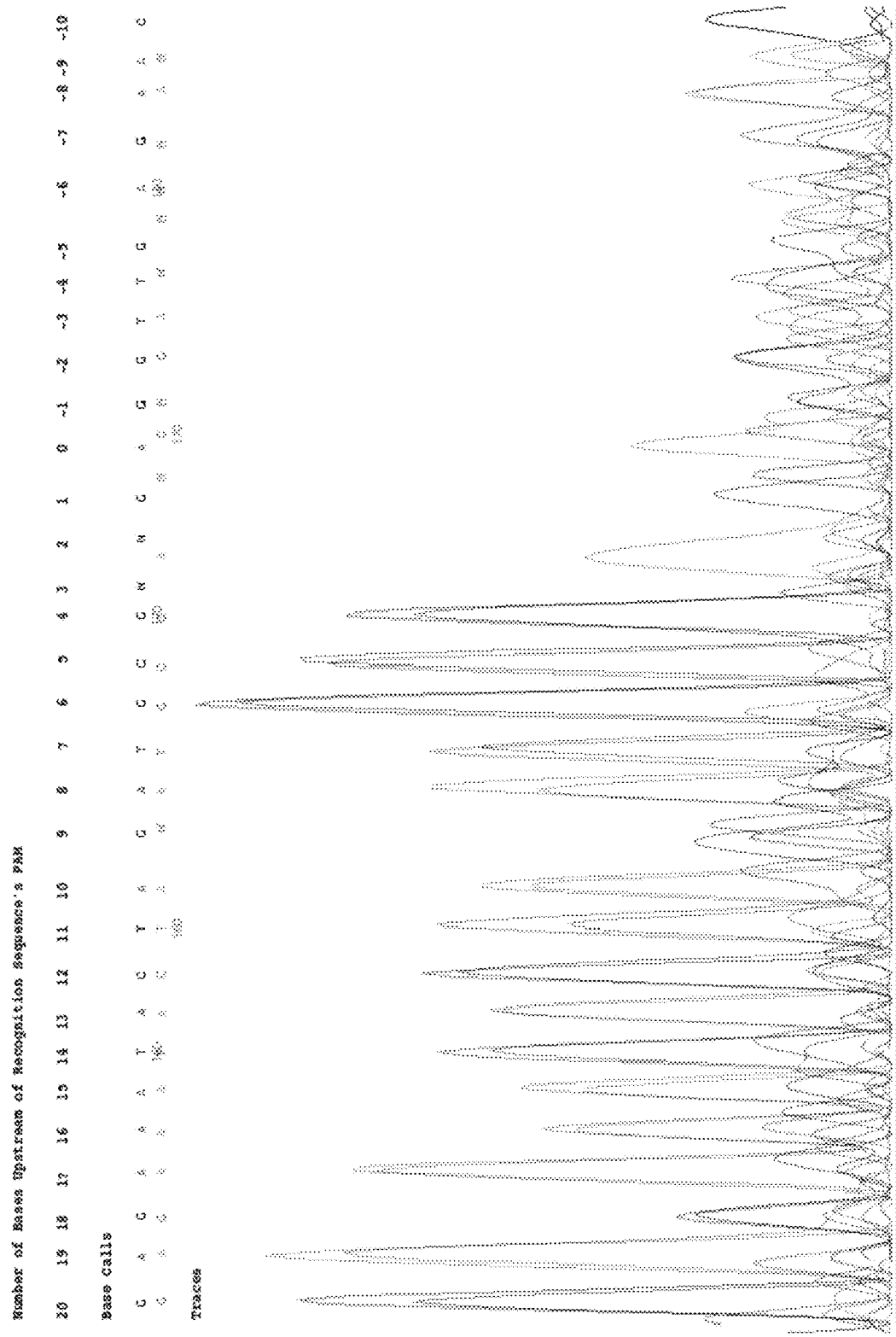
FIG. 7 depicts Sanger sequencing trace files indicating accurate base calling along the recognition sequence up until the position where Cas9 cleavage is expected. Figure discloses SEQ ID NOS 7-8, respectively, in order of appearance.

Cas9 and inducible guide RNA were cloned into BL21 *E. coli*, a strain that naturally lacks these CRISPR components. The *E. coli* also included the gene for green florescent protein (GFP), from which a subsequence was selected for the recognition sequence of the guide RNA. The constitutive T7 promoter was used for constant expression of Cas9 and GFP. The sugar-inducible pBAD promoter was used for expression of guide RNA in response to relative concentrations of arabinose and glucose. Bacteria were grown in minimal media supplemented with 0.01% arabinose and harvested in 5 minute intervals from a timecourse lasting 15 minutes. Mutation of the GFP locus over time was observed both by optical inspection of fluorescence loss and by DNA sequencing of the recognition sequence. Results are shown in FIGS. 5-7.

Example 2

Figure 8:
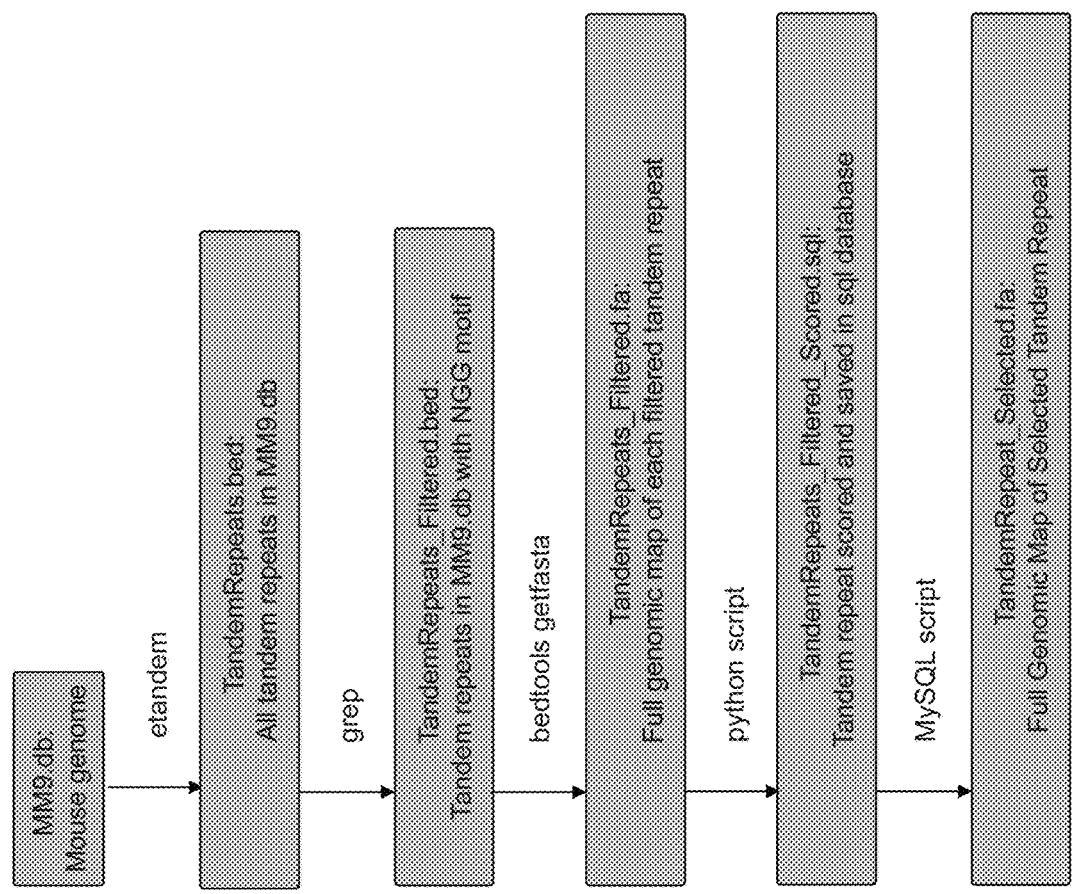
FIG. 8 is a schematic representation of an algorithm for selecting native repeat sequences for suitable CRISPR/Cas9 recognition sequence.
Figure 9:
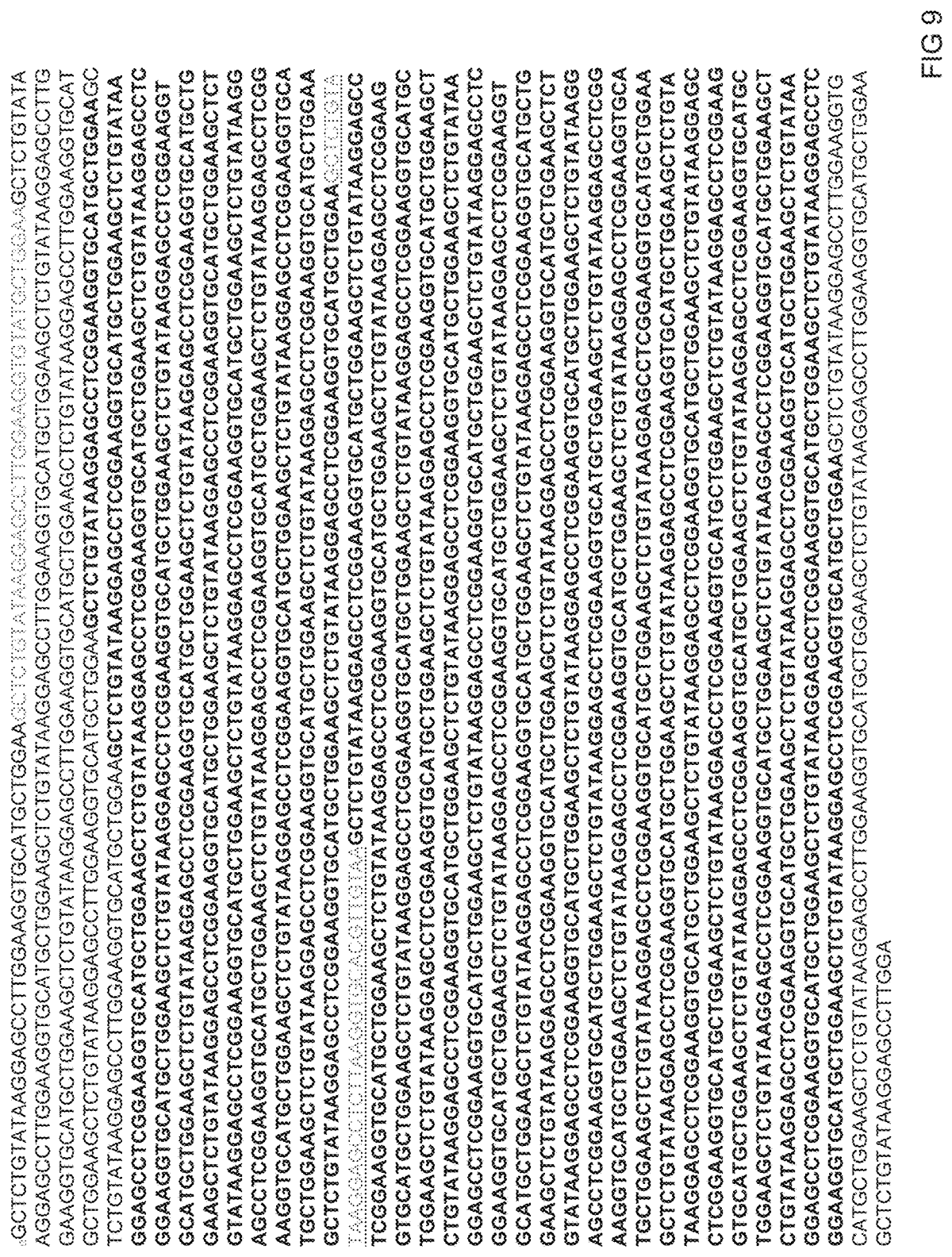

Referring to FIGS. 8 and 9, starting with the MM9 mouse genome database, a custom algorithm was applied for selecting tandem repeats sequences with repeats containing a CRISPR PAM motif.

Figure 10:
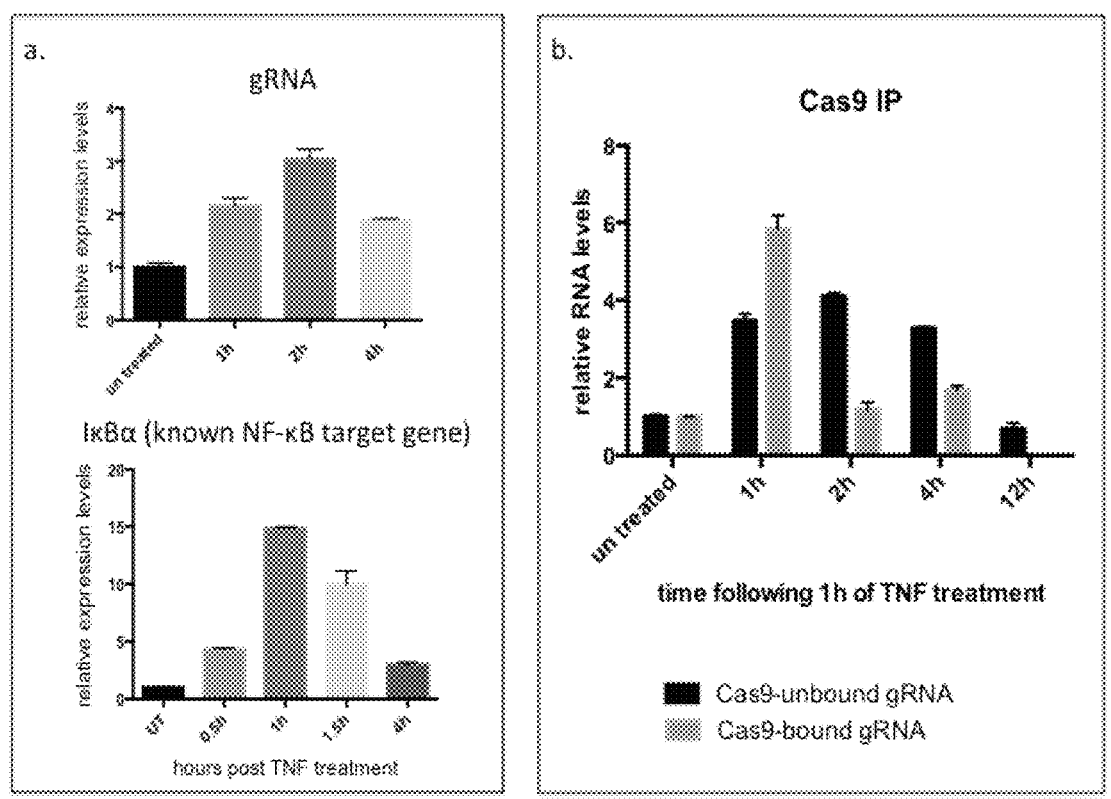
FIG. 10a. Top: NF-κB derived guideRNA expression levels in MEFs, measured by qPCR following 1 hour of TNF treatment and wash (the 1 h time point was collected at the end of the treatment). Bottom: expression levels of IκBα, a known endogenous NF-κB target gene, are shown. b. MEFs were collected at the indicated time points following an hour of TNF treatment; Cas9 was immunoprecipitated using anti-Flag beads and bound and unbound fractions were collected. RNA was purified from both fractions and analyzed by qPCR. All RNA levels were normalized to endogenous U6 shRNA.

Referring to FIG. 10, mouse embryonic fibroblast (MEF) cells were co-infected with mammalian-optimized Cas9 under constant expression by the CMV promoter and guide RNA under either constant expression by the RNA polymerase III U6 promoter or inducible RNA polymerase II NF-κB promoter. The guide RNA was designed to target the selected repetitive genomic sequence.

Figure 11:
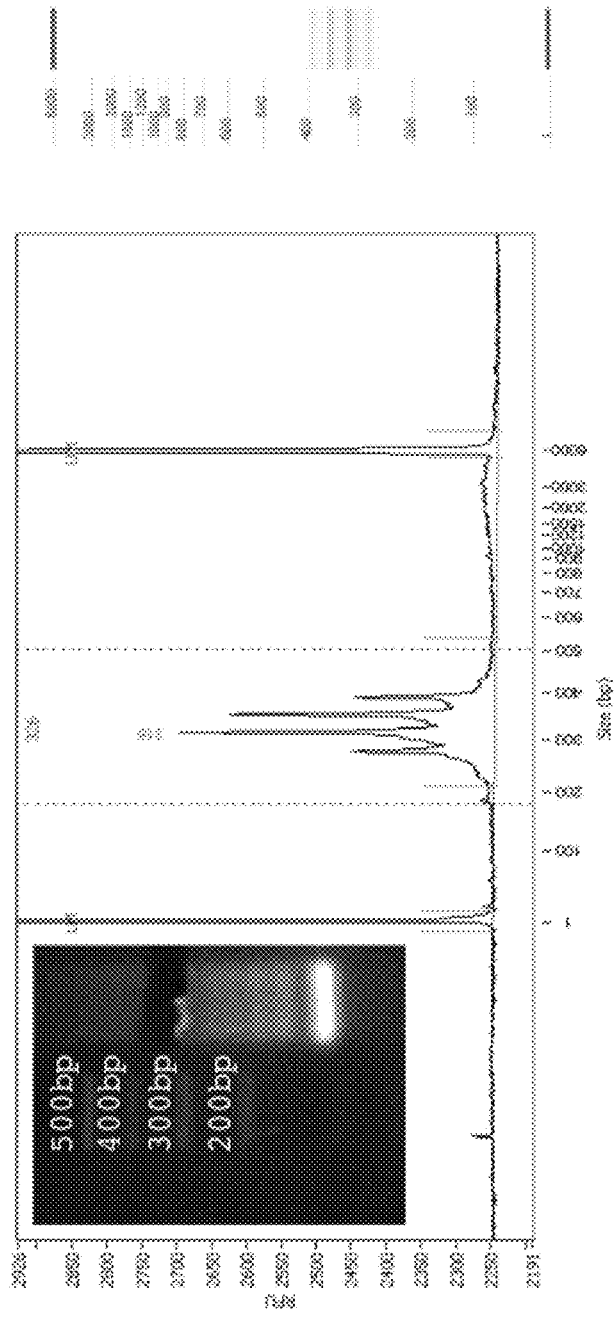
FIG. 11 Top: Primer design used in an initial round of PCR amplification for DNA sequencing preparation. Primer sequences were selected internally from the repeat sequence with tails adding part of the sequencing adapter. Bottom Inset: Agarose gel imaged after size selection of amplicons containing more than 5 repeats. Bottom: Fragment analysis on the size selected extract. Figure discloses SEQ ID NOS 10-11 and 11-12, respectively, in order of appearance.
Figure 12:
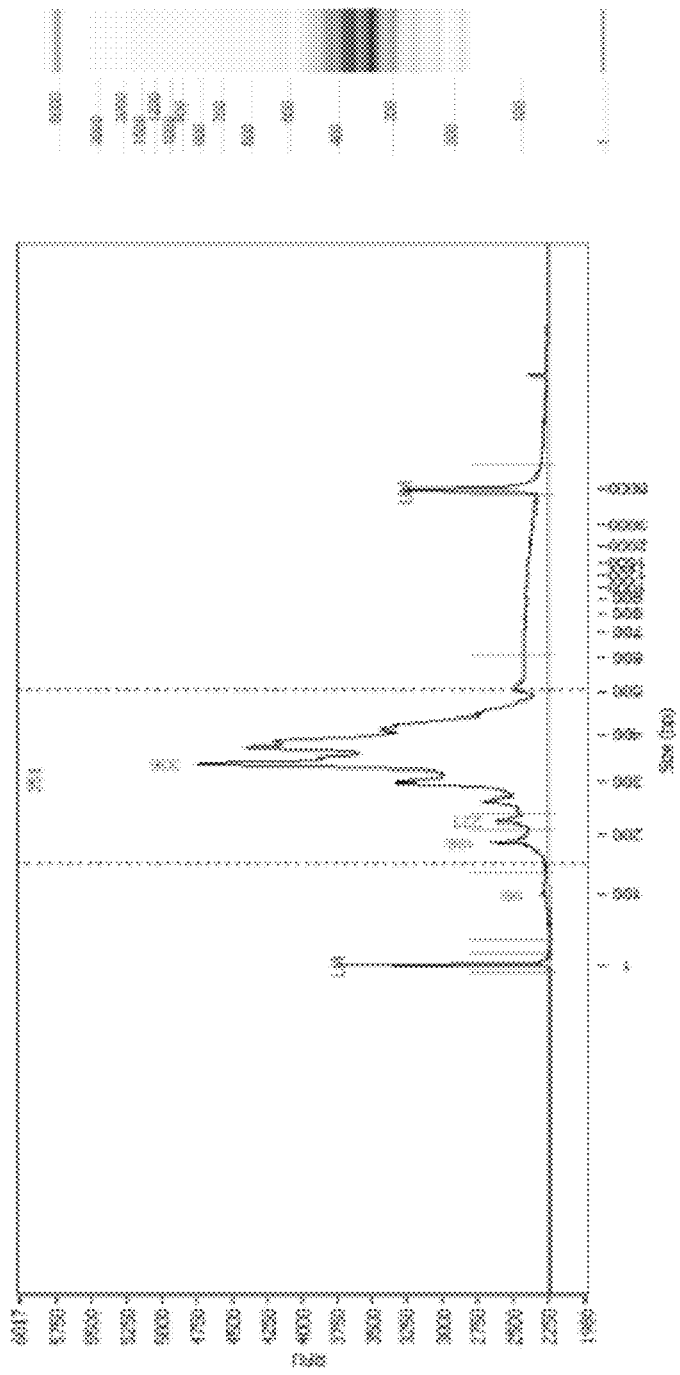
FIG. 12 Top: Primer design used in a second round of PCR amplification for DNA sequencing preparation that adds the remainder of adapter sequence along with library barcodes. Bottom Inset: Agarose gel imaged after size selection. Bottom: Fragment analysis on the size selected extract.
Figure 14:
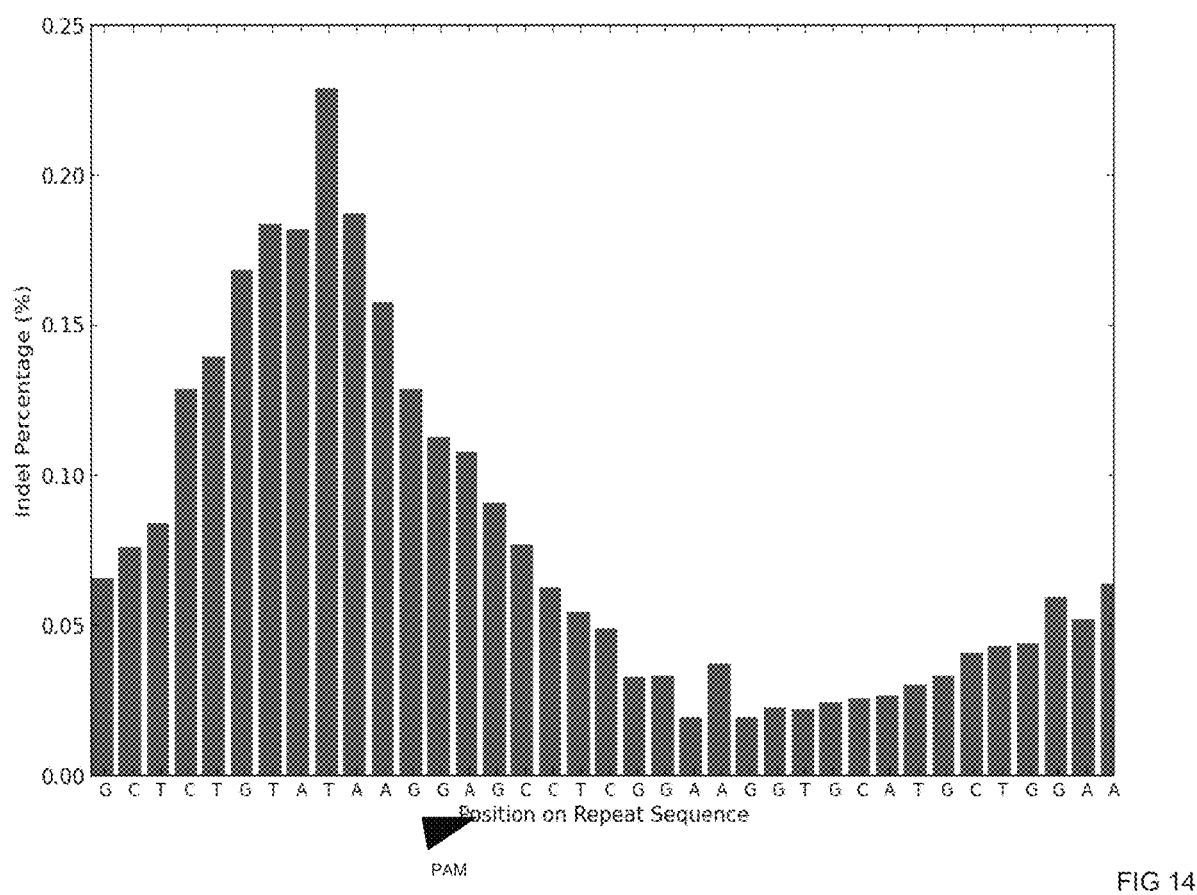
FIG. 14 depicts a histogram of indel percentage observed along the repeat sequence (SEQ ID NO: 11) after one week of U6 driven expression of guide RNA. As expected, the peak is positioned at the site of Cas9 cleavage.
Figure 15:
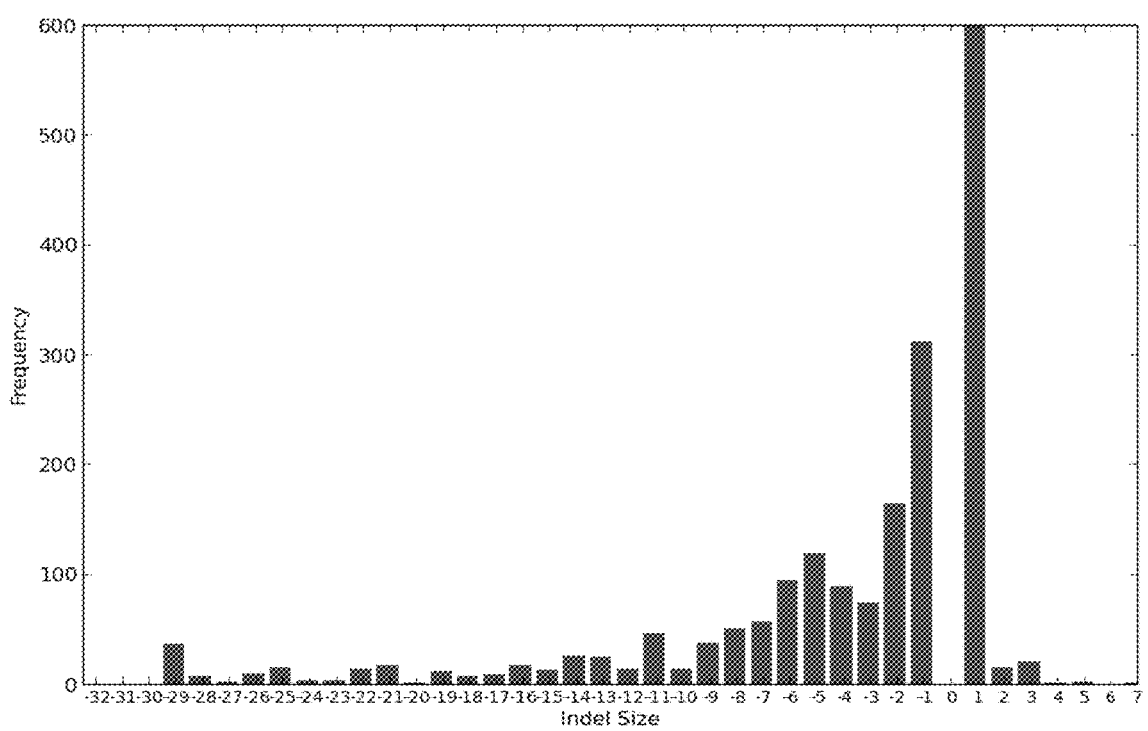
FIG. 15 depicts a histogram of indel sizes observed after one week of U6 driven expression of guide RNA. Consistent with many studies, a majority of mutations are either a one base deletion or insertion.
Figure 16:
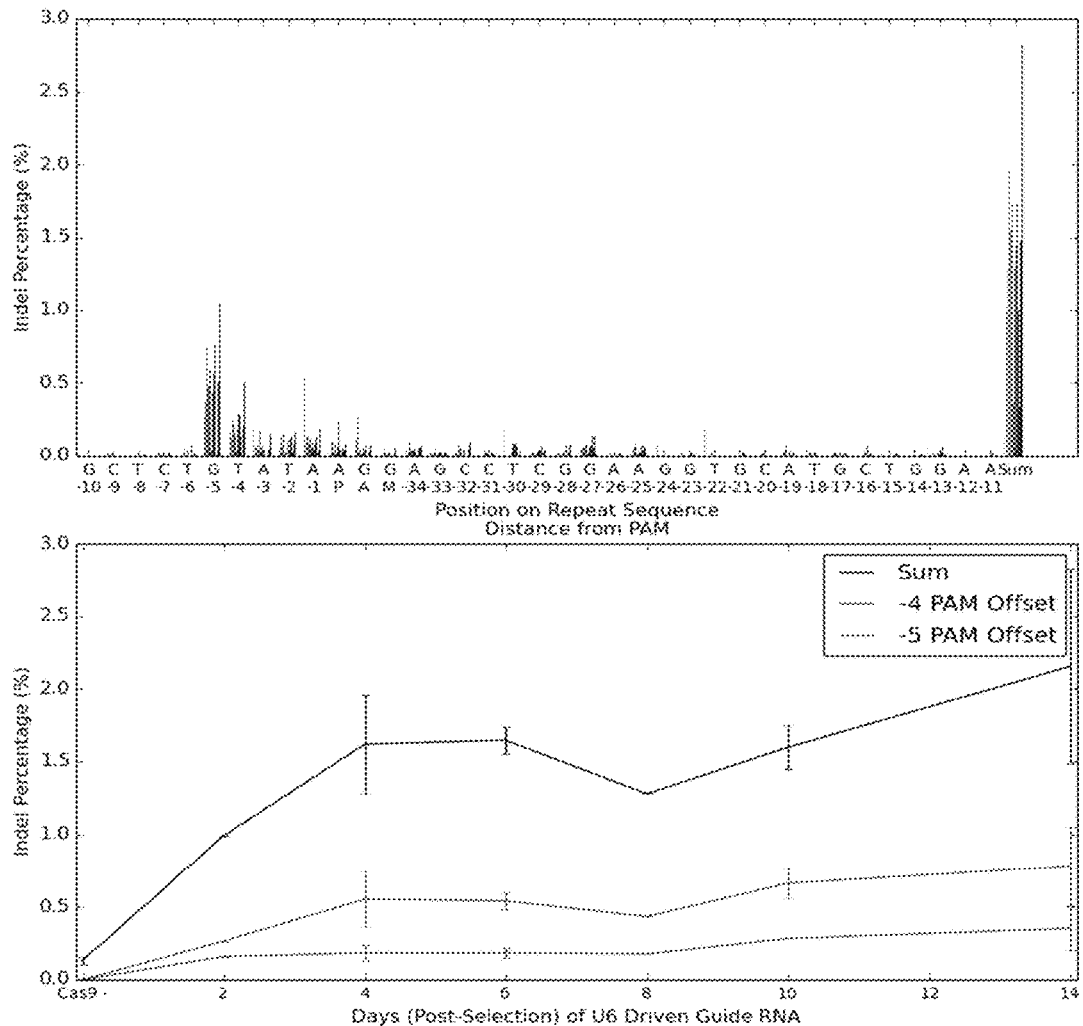
FIG. 16 Top: Adjoined histograms of indel percentage observed along the repeat sequence (SEQ ID NO: 11) for a two week timecourse of U6 driven expression of guide RNA. Time points are displayed from left to right for each position on the repeat. As expected, the peak is positioned at the site of Cas9 cleavage. Bottom: Plot of indel percentage observed along the repeat sequence for a two week timecourse of U6 driven expression of guide RNA.

Referring to FIGS. 11 and 12, MEFs infected with U6 driven guide RNA and constitutive Cas9 were harvested every other day for 14 days. Their DNA was then purified and the genomic area containing the repetitive sequence was amplified and sequenced on an Illumina MiSeq.

Referring to FIGS. 13 through 16, indels were quantified for all libraries in the sequencing data by matching a sliding window on the reads with pre-populated lookup tables of expected sequences for each indel possibility within the window. Matches to the lookup tables also pointed to the indel size. If no close matches were found, then the search on the read would halt. Otherwise, the indel position and size was tallied and the window would continue its slide to the next position on the read.

Figure 17:
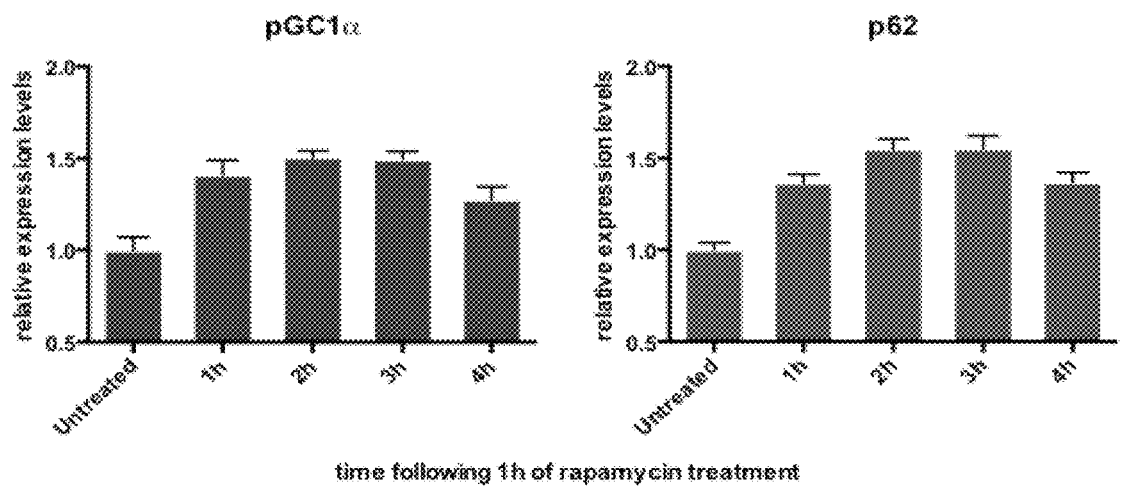
FIG. 17 Left: TFEB-derived guideRNA expression levels in MEFs, under the regulation of the pGC1α promoter, measured by qPCR following 1 hour of rapamycin treatment and wash (the 1 h time point was collected at the end of the treatment). Right: expression levels of p62, a known endogenous TFEB target gene, are shown.

Referring to FIG. 17, mouse embryonic fibroblast (MEF) cells were also co-infected with mammalian-optimized Cas9 under constant expression by the CMV promoter and guide RNA under the inducible RNA polymerase II promoter pGC1α. Again, the guide RNA was designed to target the selected repetitive genomic sequence.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A cell-based genomically encoded memory data sensing and recording system for determining the presence of at least one signal originating from outside or inside of a cell, the system comprising:
   (i) a cell comprising at least one nucleic acid sequence encoding at least one directed endonuclease specific to at least one target sequence, wherein the target sequence is a synthetic non-natural or heterologous of repeats located on a plasmid within the cell, or natural, non-essential sequence selected from tandem repeat sequences, repetitive sequences, or distributed repeat sequences located within the cell, and wherein said directed endonuclease is selected from Zinc Finger Nucleases (ZFNs), Transcription Activator Like Effector Nucleases (TALENs), and the Clustered Regularly Interspaced Palindromic Repeats (CRISPR) system; and
   (ii) at least one inducible promoter operably linked to said at least one directed endonuclease, said promoter responsive to the at least one signal of interest;
   wherein upon inducement of the promoter in response to the signal, the promoter causes expression of the directed endonuclease wherein the expressed directed endonuclease binds to, and cuts the target sequence located within the cell, and wherein the repair of the target sequence introduces at least one error in the target sequence, the presence of the at least one error in the target sequence indicative that the cell was exposed to the at least one signal of interest.

2. The system of claim 1, wherein the at least one promoter operably linked to the at least one nucleic acid sequence encoding the directed endonuclease is part of a vector system.

3. A cell-based data sensing and recording system for determining the presence of at least one signal originating from outside or inside of a cell, the system comprising a cell comprising a vector system comprising one or more vectors; wherein the vector system comprises
   (a) at least one first promoter operably linked to one or more guide RNAs specific to at least one target sequence, wherein the target sequence is a synthetic non-natural or heterologous sequence of repeats located on a plasmid within the cell, or natural, non-essential sequence selected from tandem repeat sequences, repetitive sequences, or distributed repeat sequences located within the cell; and
   (b) at least one second promoter operably linked to at least one sequence encoding a CRISPR enzyme,
   provided that at least one of the first promoter or second promoter is an inducible promoter responsive to the at least one signal of interest; and
   wherein upon inducement of the inducible promoter in response to the signal, the CRISPR enzyme binds to and cuts the target sequence located within the cell, and wherein the repair of the target sequence introduces at least one error in the target sequence, the presence of the at least one error in the target sequence indicative that the cell was exposed to the at least one signal of interest.

4. The system of claim 3, wherein components (a) and (b) are located on the same vector.

5. The system of claim 3, wherein components (a) and (b) are located on different vectors.

6. The system of claim 3, wherein the vector system comprises (a) two or more guide RNAs operably linked to different inducible promoters and (b) at least one promoter operably linked to at least one sequence encoding a CRISPR enzyme.

7. The system of claim 6, wherein the different inducible promoters respond to different physical and/or chemical signals.

8. The system of claim 3, wherein the vector system comprises (a) one or more guide RNAs operably linked to at least one promoter and (b) two or more sequences encoding a CRISPR enzyme operably linked to different inducible promoters.

9. The system of claim 8, wherein the different inducible promoters respond to different physical and/or chemical signals.

* * * * *